(12) United States Patent
Maltezos et al.

(10) Patent No.: US 8,187,541 B2
(45) Date of Patent: May 29, 2012

(54) APPARATUS FOR DETECTING TARGET MOLECULES AND RELATED METHODS

(75) Inventors: George Maltezos, Fort Salonga, NY (US); Jeremy Witzens, Del Mar, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 158 days.

(21) Appl. No.: 11/856,722

(22) Filed: Sep. 18, 2007

(65) Prior Publication Data

US 2008/0069733 A1 Mar. 20, 2008

Related U.S. Application Data

(60) Provisional application No. 60/845,336, filed on Sep. 18, 2006.

(51) Int. Cl.
| | |
|---|---|
| G01N 21/00 | (2006.01) |
| G01N 21/01 | (2006.01) |
| G01N 21/76 | (2006.01) |
| G21K 5/00 | (2006.01) |
| C25B 13/00 | (2006.01) |
| G01N 33/48 | (2006.01) |
| F17D 1/16 | (2006.01) |
| F17D 3/00 | (2006.01) |
| G01J 3/30 | (2006.01) |
| G01B 9/02 | (2006.01) |

(52) U.S. Cl. ........... 422/82.05; 422/82.06; 436/63; 436/164; 436/172; 137/14; 137/829; 204/603; 250/458.1; 356/39; 356/317; 356/337; 356/436; 356/491

(58) Field of Classification Search ............... 422/82.05
See application file for complete search history.

(56) References Cited

U.S. PATENT DOCUMENTS

| | | | |
|---|---|---|---|
| 4,615,855 A | 10/1986 | Orlowski et al. | |
| 5,176,864 A | 1/1993 | Bates et al. | |
| 5,228,923 A | 7/1993 | Hed | |
| 5,381,848 A | 1/1995 | Trabucco | |
| 5,740,051 A | 4/1998 | Sanders et al. | |
| 5,997,796 A | 12/1999 | Moore | |
| 6,068,801 A | 5/2000 | Bodo et al. | |
| 6,074,725 A | 6/2000 | Kennedy | |
| 6,136,212 A | 10/2000 | Mastrangelo et al. | |
| 6,193,471 B1 | 2/2001 | Paul | |
| 6,302,134 B1 * | 10/2001 | Kellogg et al. | 137/74 |

(Continued)

OTHER PUBLICATIONS

Kartalov, Emil P. et al "Microfluidic device reads up to four consecutive base pairs in DNA sequencing-by-synthesis" in Nucleic Acids Research, 2004, 32 (9). pp. 2873-2879.

(Continued)

*Primary Examiner* — In Suk Bullock
*Assistant Examiner* — Jennifer Wecker
(74) *Attorney, Agent, or Firm* — Steinfl & Bruno LLP

(57) ABSTRACT

An apparatus for analysis of a sample and in particular of a biological sample. The apparatus contains a microfluidic chip with dies, adapted to be selectively activated or deactivated by presence of target molecules in the biological sample. The apparatus further contains a light source to emit light for illumination of the microfluidic chip and an optical filter to allow passage of the light from the dies once activated or deactivated by the presence of the target molecules. A method for pressurizing a microfluidic chip is also disclosed, where a chamber is provided, the chamber is connected with the microfluidic chip and pressure is applied to the chamber.

16 Claims, 14 Drawing Sheets

U.S. PATENT DOCUMENTS

| | | | |
|---|---|---|---|
| 6,512,236 B2* | 1/2003 | Seville | 250/458.1 |
| 6,786,591 B2 | 9/2004 | Dunfield et al. | |
| 6,875,619 B2 | 4/2005 | Blackburn | |
| 6,929,030 B2 | 8/2005 | Unger et al. | |
| 7,169,560 B2 | 1/2007 | Lapidus et al. | |
| 7,201,836 B2 | 4/2007 | Vogel et al. | |
| 7,221,455 B2* | 5/2007 | Chediak et al. | 356/419 |
| 7,265,833 B2 | 9/2007 | Oldham et al. | |
| 7,473,397 B2* | 1/2009 | Griffin et al. | 422/504 |
| 7,480,042 B1 | 1/2009 | Phillips et al. | |
| 7,854,897 B2* | 12/2010 | Tanaami et al. | 422/505 |
| 2001/0045358 A1 | 11/2001 | Kopf-Sill et al. | |
| 2002/0108660 A1 | 8/2002 | Braun et al. | |
| 2002/0195152 A1* | 12/2002 | Fernandes et al. | 137/803 |
| 2003/0000835 A1 | 1/2003 | Witt et al. | |
| 2003/0015425 A1 | 1/2003 | Bohm et al. | |
| 2003/0160957 A1* | 8/2003 | Oldham et al. | 356/317 |
| 2003/0175987 A1* | 9/2003 | Verdonk et al. | 436/172 |
| 2003/0215941 A1 | 11/2003 | Campbell et al. | |
| 2003/0232203 A1 | 12/2003 | Mutlu et al. | |
| 2003/0235924 A1 | 12/2003 | Adams et al. | |
| 2004/0132218 A1 | 7/2004 | Ho | |
| 2004/0249227 A1 | 12/2004 | Klapproth et al. | |
| 2005/0026301 A1* | 2/2005 | Petithory | 436/180 |
| 2005/0191620 A1 | 9/2005 | McDevitt et al. | |
| 2006/0068490 A1* | 3/2006 | Tang et al. | 435/287.2 |
| 2006/0204699 A1 | 9/2006 | Maltezos et al. | |
| 2006/0222569 A1* | 10/2006 | Barten et al. | 422/100 |
| 2006/0241514 A1* | 10/2006 | Davies | 600/547 |
| 2006/0250616 A1* | 11/2006 | Pettipiece et al. | 356/456 |
| 2006/0263818 A1 | 11/2006 | Scherer et al. | |
| 2006/0288708 A1 | 12/2006 | Maltezos et al. | |
| 2007/0012891 A1 | 1/2007 | Maltezos et al. | |
| 2007/0045880 A1 | 3/2007 | Rajagopal et al. | |
| 2007/0225922 A1* | 9/2007 | Foss et al. | 702/45 |
| 2007/0266801 A1* | 11/2007 | Khademhosseini et al. | 73/863.91 |
| 2008/0013092 A1 | 1/2008 | Maltezos et al. | |
| 2008/0025888 A1* | 1/2008 | Gotzen | 422/241 |
| 2008/0044887 A1 | 2/2008 | Maltezos et al. | |
| 2008/0069733 A1 | 3/2008 | Maltezos et al. | |
| 2008/0083465 A1 | 4/2008 | Maltezos et al. | |
| 2008/0133267 A1 | 6/2008 | Maltezos et al. | |
| 2008/0142157 A1 | 6/2008 | Maltezos et al. | |
| 2008/0145286 A1 | 6/2008 | Maltezos et al. | |
| 2008/0190830 A1 | 8/2008 | Maltezos et al. | |
| 2008/0219891 A1* | 9/2008 | McDevitt et al. | 422/82.05 |
| 2009/0152215 A1* | 6/2009 | Ahn et al. | 210/808 |
| 2009/0171236 A1* | 7/2009 | Davies | 600/547 |

OTHER PUBLICATIONS

Unger Marc A. et al. "Monolithic Microfabricated Valves and Pumps by Multilayer Soft Lithography", in Science, Apr. 7, 2000, vol. 288. No. 5463, pp. 113-116.

Kartalov, Emil P. et al High-throughput multi-antigen microfluidic fluorescence immunoassays in Biotechniques 2006, vol. 40, No. 1: pp. 85-90.

Piyasena Menake E., et al. "Near-Simultaneous and Real-Time Detection of Multiple Analytes in Affinity Microcolumns" in Anal. Chem. 2004, 76, 6266-6273.

Hernandez L. et al. "Determination of Binding Constants of Polyethylene Glycol Vancomycin Derivatives to Peptide Ligands Using Affinity Capillary Electrophoresis" in Chromatographia Mar. 2007, vol. 65, No. 5-6.

Hu Q, Zhang C, Sommerfeld M, "Biodiesel from algae: Lessons learned over the past 60 years and future perspectives", Journal of Phycology 42: 12-12 37 Suppl. 1 (Apr. 2006).

Kosourov S, Patrusheva E, Ghirardi ML, et al., "A comparison of hydrogen photoproduction by sulfur-deprived *Chlamydomonas reinhardtii* under different growth conditions", Journal of Biotechnology 128 (4): 776-787 (Mar. 10, 2007).

A.D. Stroock, S. K. Dertinger, A. Ajdari, I. Mezic, H.A. Stone, G. M. Whitesides "Chaotic Mixer for Microchannels", Science 25 vol. 295 No. 5555, pp. 647-651 (Jan. 2002).

T. You, S.M. Barnett "Effect of Light Quality on Production of Extracellular Polysaccharides and Growth Rate of *Porphyridium cruentum*", Biochem. Eng. J. vol. 19, No. 3, pp. 251-258 (2004).

C. Sorokin, R. W. Krauss "The Effects of Light Intensity on the Growth Rates of Green Algae", Plant Physiol. 33: 109-112 (1958).

Inatomi, K., S. Izuo, S. Lee, H. Ohji, S. Shiono, Electrophoresis of DNA in micro-pillars fabricated in polydimethylsiuloxane, Microelectronic Engineering, vol. 70 (2003) pp. 13-18.

PCT International Search Report for PCT/US2007/078689 filed on Sep. 18, 2007 in the name of California Institute of Technology, et al.

PCT Written Opinion for PCT/US2007/078689 filed on Sep. 18, 2007 in the name of California Institute of Technology, et al.

Basic Microfluidic Concepts, retrieved Oct. 13, 2005 from http://faculty.washington.edu/yegerp/microfluidicstutorial/basicconcepts.htm.

Chiem, N.H., et al., "Microchip-based capillary electrophoresis for immunoassays: analysis of monoclonal antibodies and theophylline", Electrophoresis 19, 3040 (1998).

Chou, H.P., et al. "A Microfabricated Rotary Pump" / Biomedical Microdevices 3, 323 (2001).

Clark, A.M., et al., Cooling of bulk material by electron-tunneling refrigerators, Applied Physics Letters 86, 173508 (2005).

Fan, X., et al., SiGeC/Si superlatice microcoolers, Applied Physics Letters, vol. 78, No. 11, pp.~1580-1583 (Mar. 12, 2001).

Fiedler, S., et al., "Dielectrophoretic sorting of particles and cells in a microsystem", Anal. Chern. 70, 1909 (1998).

Fu, A.Y. et al., "A micro fabricated fluorescence-activated cell s o r t. er " ƒ Nature Biotech. 18, 309, 309 (2000).

Godfrey, S., "Electronics Cooling: An introduction to the thermostatic *coolers*" J retrieved Oct. 10, 2005 from http://www.electronicscooling.com/Resources/EC_Articles/SEP96.

Hadd, A.G., et al., "Microchip device for performing enzyme assays", Anal. Chern. 69, 3407 (1997).

Ikuta, K., et al., "Biochemical IC chip toward cell free DNA protein synthesis", MEMS 2000, Miyakazi, Japan,pp. 131-136 (Jan. 23-27, 2000).

Ikuta, K. et al., "Fluid drive chips containing multiple pumps and switching valves for Biochemical IC Family", MEMS Heidelberg Germany, pp. 739-744 (Jan. 25-29, 1998).

Jeon, N. L. et al., Microfluidics Section: Design and Fabrication of Integrated Passive Valves and Pumps for flexible Polymer 3-dimensional Microfluidic systems, Biomedical Microdevices 4:2, pp. 117-121 (2002).

Kopp, M.U. et al. "Chemical amplification: continuous flow PCR on a chip", Science 280, 1046 (1998).

Lagally, E. T. et al., "Monolithic integrated microfluidic DNA amplification and capillary electrophoresis analysis system",Sensors and Actuators B—chemical 63 (3) : 138-146 (May 15, 2000).

Lee, J. et al., "Two Phase flow in high heat flux microcha=el heatsink for refrigeration cooling applications: Part II—heat transfer characteristics", International Journal of Heat and Mass Transfer, 48, pp. 941-955 (2005).

Lee, H., et al. "Package embedded heat exchanger for stacked multi-chip module".

Li, P.H. et al., "Transport, manipulation and reaction of biological cells on-chip using electrokinetic effect", Anal. chern 69, 1564 (1997).

Liu, J. et al., Electrophoresis, 23, 1531 (2002).

Morgan, H. et al., "Large Area travelling-wave dielctrophoresis particle seperator", Journal of Microengineering, 7, 65 (1997).

Peltier-Seebeck Effect-wikipedia, retrieved Oct. 10, 2005 from http://en.wikipedia.org/wiki/Peltier-Seebeck_effect.

"Peltier Coolers", retrieved Oct. 10, 2005 from http://www.digitlife.com/articles/peltiercoolers/.

Quake, S. R.et al, "From Micro to Nano Fabrication with Soft Materials", Science 290, 1536 (2000).

Thorsen, T. et al. "Microfluidic Large-Scale Integration", Science 298,5593 (2002).

Unger, M.A. et al. "Monolithic Microfabricated Valves and Pumps by Multilayer Soft Li thography" r Science 288, 113 (2000).

Waters, L.C. et al., "Microchips devices for cell lysis, multiplex PCR amplification, and electrophoretic s i z i nq ", Anal. Chern. 70, 158 (1998).

Wu, H.K. et al., "Fabrication of complex three-dimensional microchannel systems in PDMS", Journal of Te American Chemical Society 125 (2),pp. 554-559 (Jan. 15, 2003).

Non-Final Office Action issued on Apr. 29, 2010 by the USPTO for U.S. Appl. No. 11/804,112, filed May 17, 2007.

Brody, J., et al., Low Reynolds Number Micro-fluidic Devices, Solid State Sensor and Actuator Workshop, Hilton Head, SC Jun. 2-6, 1996.

Chiem, N., et al. Monoclonal Antibody Binding Affinity Determined by Microchip-based Capillary Electrophoresis, Electrophoresis 1998, 19: 3040-3044.

Chou, HP., et al., A Microfabricated Rotary Pump, Biomedical Microdevices 2001, 3: 323-330.

Dharmatilleke, S., et al., Three-dimensional Silicone Device Fabrication and Inter-connection Scheme for Microfluidic Applications using Sacrificial Wax Layers, Micro-Electro-Mechanical Systems 2000, 2: 413-418.

Fiedler, S., et al., Dielectrophoretic Sorting of Particles and Cells in a Microsystem, Analytical Chemistry 1998, 70: 1909-1915.

Fu, A., et al., A Microfabricated Fluorescence-activated Cell Sorter, Nature Biotechnology 1999, 17: 1109-1111.

Hadd, A., et al., Microchip Device for Performing Enzyme Assays, Analytical Chemistry 1997, 69: 3407-3412.

Hadd, A., et al., Microfluidic Assays of Acetylcholinesterase Inhibitors, Analytical Chemistry 1999, 71: 5206-5212.

Ikuta, K., et al., Biochemical IC Chip Toward Cell Free DNA Protein Synthesis, IEEE 1998, 131-136.

Ikuta, K., et al., Fluid Drive Chips Containing Multiple Pumps and Switching Valves for Biochemical IC Family, IEEE 2000, 739-744.

Jeon, N., et al., Design and Fabrication of Integrated Passive Valves and Pumps for Flexible Polymer 3-Dimensional Microfluidic Systems, Biomedical Microdevices 2002, 4: 117-121.

Kopp, M., et al., Chemical Amplifications: Continuous-flow PCR on a Chip, Science 1998, 280: 1046-1048.

Li, P., et al., Transport, Manipulation, and Reaction of Biological Cells On-chip using Electrokinetic Effects, Analytical Chemistry 1997, 69: 1564-1568.

Liu, J., et al., A Nanoliter Rotary Device for Polymerase Chain Reaction, Electrophoresis 2002, 23: 1531-1536.

Morgan, H., et al., Large-area Travelling-wave Dielectrophoresis Particle Separator, Journal of Micromechanical Microengineering 1997, 7: 65-70.

Quake, S., et al., From Micro- to Nanofabrication with Soft Materials, Issues in Nanotechnology 2000, 290: 1536-1540.

Thorsen, T., et al., Microfluidic Large-scale Integration, Science 2002, 298: 580-584.

Waters, L., et al., Microchip Device for Cell Lysis, Multiplex PCR Amplification, and Electrophoretic Sizing, Analytical Chemistry 1998, 70: 158-162.

Wu, H., et al., Fabrication of Complex Three-Dimensional Microchannel Systems in PDMS, Journal of the American Chemical Society 2003, 125: 554-559.

Non-Final Office Action issued by the USPTO for U.S. Appl. No. 11/804,112, filed May 17, 2007 in the name of Maltezos et al.; mail date: Jan. 19, 2011.

Restriction Requirement issued by the USPTO for U.S. Appl. No. 11/804,112, filed May 17, 2007 in the name of Maltezos et al.; mail date: Dec. 15, 2009.

Non-Final Office Action issued by the USPTO for U.S. Appl. No. 11/297,651, filed Dec. 7, 2005 in the name of Maltezos et al.; mail date: Nov. 14, 2008.

Notice of Abandonment issued by the USPTO for U.S. Appl. No. 11/297,651, filed Dec. 7, 2005 in the name of Maltezos et al.; mail date: Jun. 22, 2009.

Restriction Requirement issued by the USPTO for U.S. Appl. No. 11/297,651, filed Dec. 7, 2005 in the name of Maltezos et al.; mail date: Apr. 21, 2008.

Restriction Requirement issued by the USPTO for U.S. Appl. No. 11/297,651, filed Dec. 7, 2005 in the name of Maltezos et al.; mail date: Jul. 11, 2008.

Non-Final Office Action issued by the USPTO for U.S. Appl. No. 11/297,214, filed Dec. 7, 2005 in the name of Maltezos et al.; mail date: Feb. 19, 2009.

Notice of Abandonment issued by the USPTO for U.S. Appl. No. 11/297,124, filed Dec. 7, 2005 in the name of Maltezos et al.; mail date: Oct. 19, 2009.

Restriction Requirement issued by the USPTO for U.S. Appl. No. 11/297,124, filed Dec. 7, 2005 in the name of Maltezos et al.; mail date: Nov. 17, 2008.

Razavi, B. Design of analog CMOS integrated circuits, McGraw Hill 2000, pp. 427 and 440.

* cited by examiner

APPARATUS FOR DETECTING TARGET MOLECULES AND RELATED METHODS

CROSS REFERENCE TO RELATED APPLICATIONS

This application claims priority to U.S. Provisional Application entitled "Medical Diagnostic Tool", Serial No. 60/845,336 filed on Sep. 18, 2006, the disclosure of which is incorporated herein by reference in its entirety. This application may be related to U.S. application Ser. No. 11/804,112, entitled "Fluorescence Detector, Filter Device and Related Methods", filed on May 17, 2007.

TECHNICAL FIELD

The present disclosure relates to detection of target molecules and microfluidics. In particular, it relates to an apparatus for analysis of a sample and a method for pressurizing a microfluidic chip.

SUMMARY

According to a first aspect of the present disclosure, an apparatus for analysis of a sample, and in particular a biological sample, is disclosed, the apparatus comprising: a microfluidic chip containing dies; a light source to emit light for illumination of the microfluidic chip; an optical filter; and a detector to detect the light passing through the optical filter, wherein presence of target molecules in the biological sample activates and/or immobilizes a die at a position detectable by the detector, and the optical filter allows passage of the light from the dies once activated and/or immobilized by the presence of the target molecules.

According to a second aspect of the present disclosure, a method for pressurizing a microfluidic chip comprising sealed fluidic circuits is provided, comprising: providing a first chamber in the microfluidic chip; and applying pressure to the first chamber.

According to a third aspect of the present disclosure, a method to release liquids in a microfluidic circuit is provided, comprising: introducing a liquid in a first chamber inside the microfluidic circuit; sealing the chamber; connecting the first chamber to a first channel though a sacrificial membrane; providing a second chamber; connecting the second chamber to the first chamber through a second channel; and compressing the second chamber to release the liquid from the first chamber into the first channel.

Further embodiments of the present disclosure are shown, in the specification, drawings and claims of the present application.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

In the drawings.

Like reference symbols in the various drawings indicate like elements.

DETAILED DESCRIPTION

In accordance with a first embodiment thereof, the present disclosure relates to an apparatus for detecting target molecules that can be used as a diagnostic tool or apparatus to analyze biological samples, for example to detect small quantities of proteins with an Enzyme-Linked ImmunoSorbent Assay (ELISA), as well as several methods that can be applied to the apparatus, for example, in order to make it more performant, more user friendly, or more marketable. The apparatus is not restricted to ELISA, but is generally applicable to detection mechanisms based on a microfluidic chip or optical detection. Regardless of the specific biochemistry used, the applicants introduce a series of techniques that enable, amongst other things, user friendly actuation of microfluidic devices, cheap manufacturing, high sensitivity for optical detection schemes, multi-purpose usage of the tool (that is with different types of microfluidic chips and for different types of analysis) and, in medical related applications, efficient communication with doctors, insurances, pharmacies etc.

Figure 1:
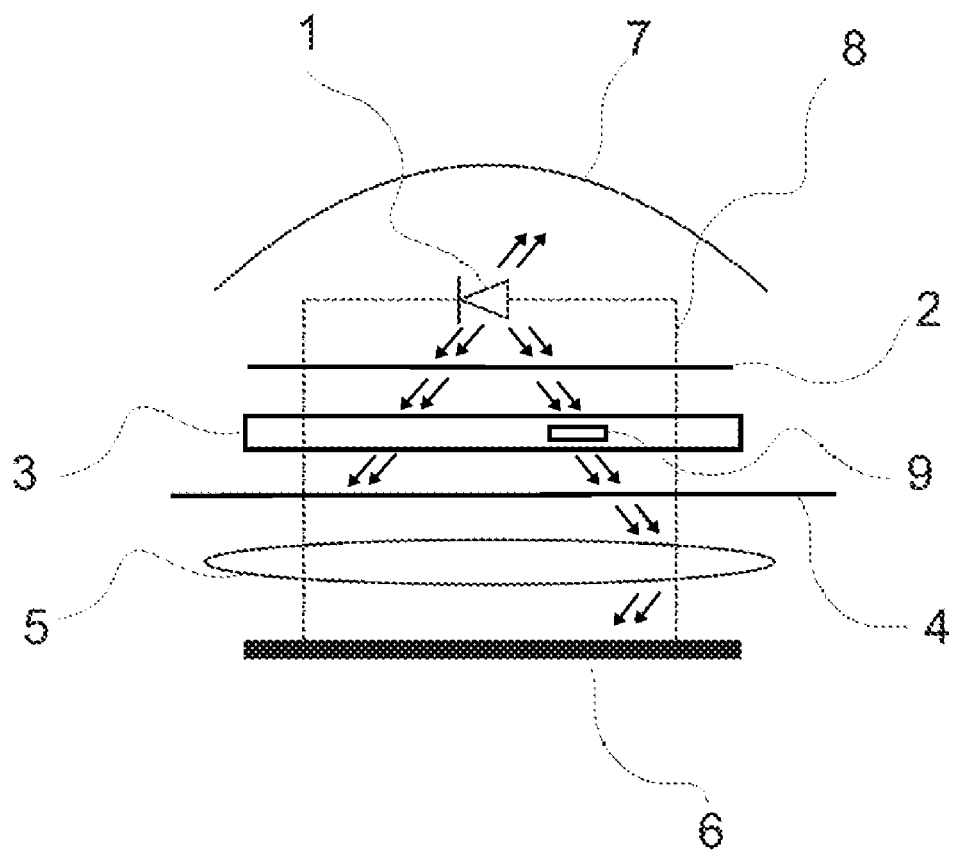
FIG. 1 is a schematic illustration of an apparatus for analysis of a sample in accordance with an embodiment of the present disclosure.

FIG. 1 shows a high-level schematic of the apparatus in accordance with the disclosure. Light is emitted from a light source (1), e.g. a bright LED or a laser diode. The light illuminates portions of a microfluidic chip or apparatus (3) that contains dies (9). Optionally, between the light source (1) and the microfluidic chip (3), an optical filter (2) can be placed that leaves the wavelength that excite the dies (9) go through but that filters out the wavelengths emitted by the dies. During the course of the biochemical analysis, the dies (9) in the microfluidic chip are selectively activated by the presence of certain molecules in the biological sample, so that emission from the dies is a quantifiable sign of the presence of these molecules. In some detection methods, presence of the target molecule modifies a sequence of events so as to activate a die (e.g. ELISA or other enzyme linked assays). However in other types of assays (for example in typical DNA microarrays or other fluorescently linked assays) the presence of the target molecule modifies a sequence of events to immobilize the die at a certain position. The mechanism of this activation is often an indirect one, where the presence of the detected molecule (the target molecule) will give rise to a series of reactions that will activate the dies. That is, the dies (9) are modified from a molecule or state in which they don't emit light or emit light that is filtered out by filter (4) to a molecule or state in which they emit light that can be transmitted through (4). In the following it will also be understood that the converse mechanism is possible. A chain of events triggered by the target molecule could also deactivate the dies. In that case the deactivation and not the activation of the die will be detected as a quantifiable signature of the target molecule.

This occurs, for example, when proteins are detected with an ELISA stack. A second optical filter (4) is ideally a notch-filter (narrow pass) that only leaves through light corresponding to the emission wavelength of the dies, or a filter that leaves through light emitted by the dies, but none of the light that is not blocked by filter (2). One or several lenses (5) can image the microfluidic circuit on a detector (6) such as a CCD or a CMOS imager. In some embodiments, a photodiode, a charge coupled device, a phototransistor or a photomultiplier tube can also be used. Optionally, reflectors (7) can be included in the apparatus to reflect back light that would otherwise not be absorbed by the dies (for example dichroic mirrors), in order to excite them with as much light as possible. The light source (1) can be modulated, for example by means of electric direct modulation, or by using a mechanical device such as a chopper, or by using another type of external modulator such as for example a Pockels Cell. A lock-in amplifier (not shown in FIG. 1) can then be used to detect signals with very bad signal to noise ratios. The lock-in amplifier can be on the same chip as the detector (6), for example if the detector is a CMOS imager and the lock-in made in CMOS technology. The same chip can also electrically modulate the light source through connection (8).

The apparatus herein described can comprise other elements, some of which are described in details herein below. In particular, in some embodiments the apparatus is very compact and, in embodiments wherein a diagnostic analysis is desired, can take the form of a hand-held diagnostic tool.

In particular, in some embodiments, the apparatus provides the means for patients to monitor the emergence of medical conditions such as cancers or other diseases, as well as to monitor the development of a known condition, or the results from a treatment, by monitoring specific molecules such as proteins in biological samples such as blood or saliva. The apparatus can be at the patients' home so that these tests can be made more frequently, more conveniently and at a smaller cost than if the patient had to go to a specialized laboratory every time. This is frequently described as personalized medicine.

The embodiments of the diagnostic device herein described can comprise means to access an Internet portal or a remote server. In those embodiments, data can be exchanged between the apparatus and the Internet/Remote Server, for example by means of either:

a dial-up or other internet modem (cable, DSL etc.) directly incorporated into the tool.
  an Ethernet port incorporated into the tool that permits plugging the tool into a local area network (LAN).
  a Wi-Fi or other wireless device incorporated in the apparatus that enables connectivity with a LAN.
  a Blue-Tooth connection or another wireless protocol incorporated into the apparatus that enables the apparatus to communicate with a computer or with a cell phone. The computer or the phone then provide the connectivity to the Internet or to the remote server.
  a connection with a computer for example by means of a USB port or other ports/protocols that enable data transfer such as Ethernet, Firewire etc. The computer then provides the connectivity to the Internet or to the remote server.
  a connection that enables the exchange of data with a phone. The phone then provides the connectivity to the Internet or to the remote server.

In some embodiments, the portal can enable the patient's doctor to access remotely the results of the diagnostic tests. In some embodiments the portal can also permit the doctor and the patient to obtain information about drugs relating to specific medical conditions. In some embodiments, advertisements for relevant drugs can be posted through the portal. In some embodiments, the portal enables large-scale data-collection over large population of patients. This data-collection can be used for example to evaluate medical trials or for statistical purposes by entities such as insurances or public-health organizations. The portal can guarantee the privacy of the patient during such data-collection by compiling the data and only delivering a compiled report, devoid of private information, to the receiver of the report. In some embodiments, the portal can also enable patients and doctors to order drugs or buy other health related items online, such as books covering the topic etc. In some embodiments, the portal can be used to send patients reminders about scheduling of health related items (such as taking your medicine or going to see your doctor), it could warn the patient that a potentially critical condition (detected by the diagnostic device) warrants a visit to a doctor. The agenda functionality would be particularly powerful if the patient needs or wishes to use the diagnostic device on a regular basis, but also needs or wishes to take care of other health related tasks that are either infrequent or very diverse. In some embodiments, the portal can enable other communication channels between the patient, the doctor, the insurance, the pharmaceutical industry, drug distributors and other providers of health care related items and services.

The portal might be used also to exchange communications between users in embodiments wherein the target detection is associated with non-medically related uses of the device herein described. A skilled person will be able to identify the non-medical related embodiments of the portal herein described, which will not be described herein in detail.

In some embodiments the apparatus includes a detector array There are many advantages of using a detector array, such as a CCD array or a CMOS imager, rather than a single photodetector or a small number of photodetectors. For example, with a detector array the position on the microfluidic chip from which the light originates can be determined. Therefore, several different types of tests can be done on the same microfluidic chip even if they all activate dies emitting at the same wavelength. The discriminating information is then provided by spatial location, that is depending where on the imager the fluorescing dies are imaged provides the apparatus with the information which protein has been detected. For example, when an ELISA stack is used to detect proteins, different proteins can be detected with different antigen or antibodies, but the stack corresponding to the detection of different molecules can activate the same die.

In some embodiments wherein a large number of pixels is involved, each individual pixel can be connected to its own amplifier (e.g. a lock-in amplifier). In some embodiments wherein a large number of pixels is involved a circuit that would otherwise be duplicated for each pixel can be divided into several pieces or stages, with a first circuit piece duplicated for each pixel ad a second circuit piece common to all or large group of pixels. A further advantage associated with the circuit division is that it enables to minimize the duplication of electronics, with minimal impact on the chip size, routing and pixel responsivity while leaving crucial elements at each pixel. For example, it is beneficial to integrate the signal of a pixel for a long time so as to accumulate the signal but cancel out the noise (the noise grows as a random walk and as such has a much slower accretion rate, so that the signal to noise ratio increases over time). Moreover, it is beneficial to accumulate each individual signal independently so that high signal to noise data can be collected for all the pixels before it is known to the chip which signals are relevant. Furthermore, propagating a signal through the optical detector chip can cause the signal to noise to degrade due to parasitic coupling to other parts of the chip and due to the high capacitive load seen an amplifier located at the end of the line. However, in a lock-in configuration, where the signal is not DC but centered around a carrier frequency, it is not possible to accumulate the signal before mixing (demodulation) because it will average out to zero. After mixing, the signal is converted to a DC component that can be accumulated. Furthermore, if a DC component is propagated through the chip rather than an AC component, capacitive coupling becomes much less of an issue. For these reasons, it is beneficial to incorporate at least the mixer, and possibly an integrating element such as a capacitor, into each pixel. This can be done for example by adding a switched capacitor, mixed-signal integrator to each pixel. Moreover, such method is compatible with a CMOS process.

As anticipated above, in order to detect molecules with very low concentration in a sample and in particular in a biological sample, lock-in amplifiers can be used. Lock-in amplifiers can recover a signal even in the presence of an overwhelming noise background, thus extremely low signals that would otherwise be lost in the noise can be recovered.

Figure 2:
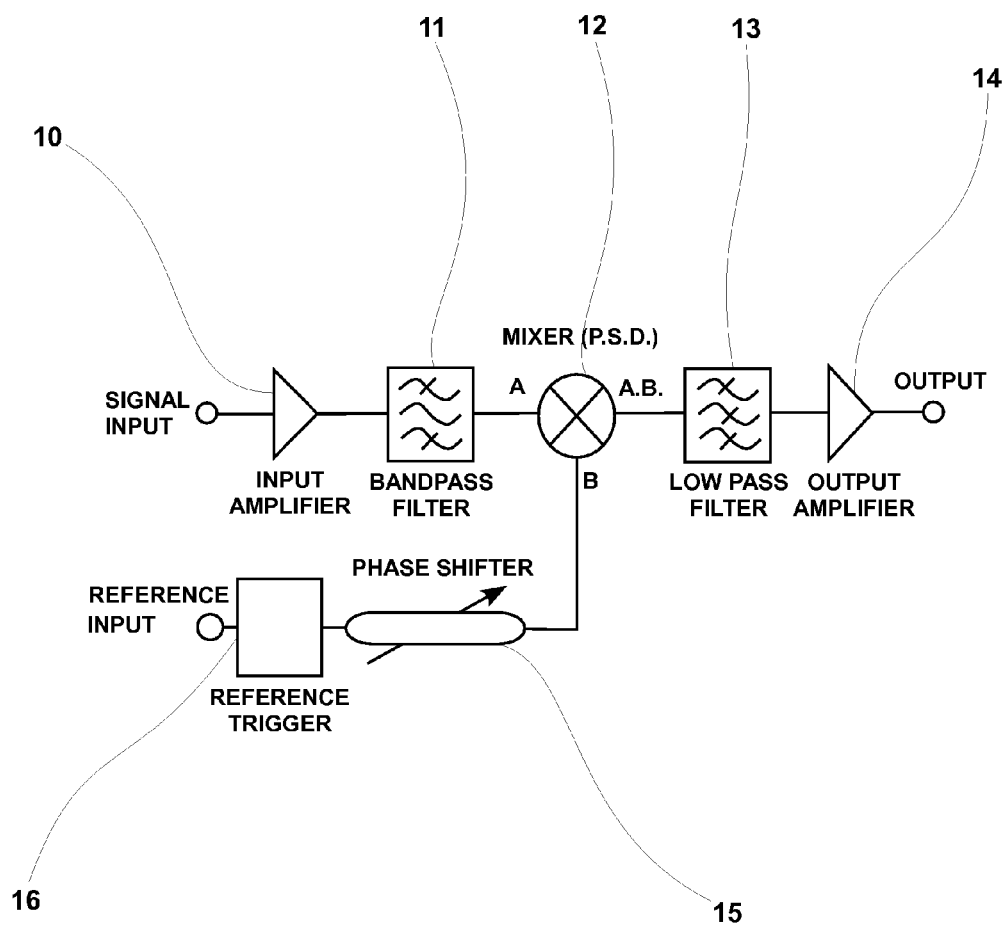
FIG. 2 shows an example of a lock-in amplifier to be used together with the apparatus of FIG. 1.

A lock-in amplifier is shown in FIG. 2 and comprises at least a mixer (12), a low-pass filter (13) and an amplifier (10) or 14). An additional bandpass filter (11) is usually present. The mixer (12) uses a reference signal at the same frequency and the same phase as the input signal. If the input signal and the reference signal are out of phase, a phase shifter (15) shifts the reference signal and the input signal back in phase. This can happen, for example, if the electrical signal that drives the light source experiences a significant phase delay before arriving at the light source, or if fluorescence lifetime imaging microscopy is implemented. Alternatively to a phase delay, a dual phase lock-in amplifier can be used.

Figure 3A:
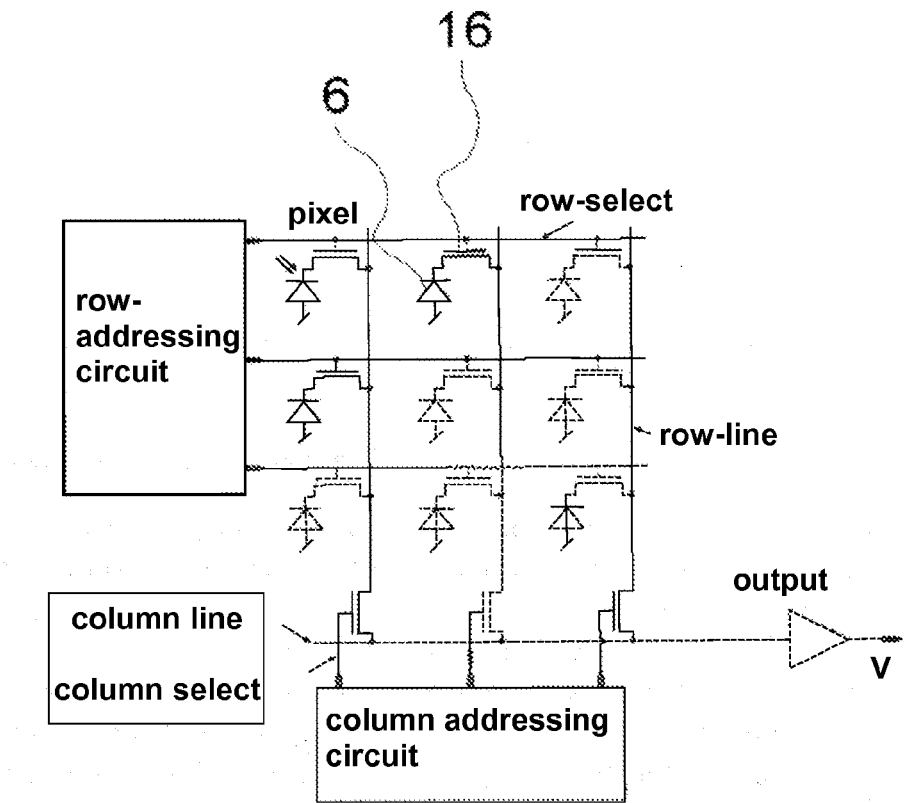
FIGS. 3A and 3B show a schematic illustration of a passive CMOS pixel array (FIG. 3A) and active CMOS pixel array (FIG. 3B) to be used as imagers in the embodiment of FIG. 1.
Figure 3B:
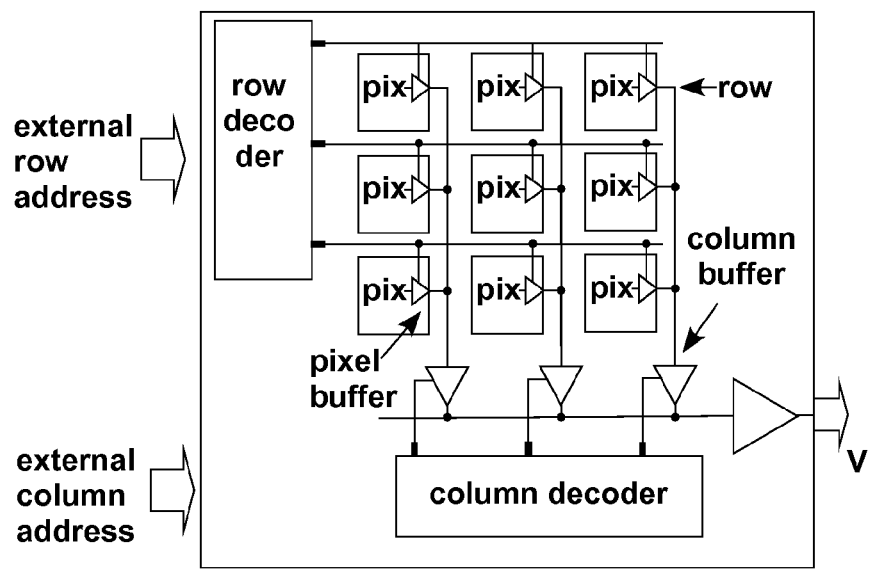

FIG. 3A shows a passive CMOS array, where a simple transistor (16) typically acts as a switch to connect a pixel to a column read-out line and then to a column buffer in the column decoder. FIG. 3B shows an active CMOS array where the simple switch transistor is replaced by a preamplifier (15). These active CMOS arrays have been shown to lead to better signal to noise ratios and are the most commonly occurring CMOS imager. The concept of active CMOS arrays can be generalized to include parts of the lock-in amplifiers. In particular, for the purpose of the apparatus of the present disclosure, the pixels do not need to be very small, so that some more circuitry can be added to each pixel without significantly reducing the ratio of the pixel size covered by the photodiode (that is without significantly reducing the sensitivity).

A part of the lock-in amplifier can be distributed throughout the CCD array or the CMOS imager. For example, the mixer (12) (see FIG. 2) can be distributed throughout the CCD or the CMOS imager, so that each individual photodiode, or local group of photodiodes, is connected to its own mixer. Other parts of the lock-in amplifier such as filters and amplifiers can also be added to each pixel. It is preferential to use a circuit compatible with a cheap CMOS process. The mixer can be implemented with either an analog multiplier, a digital switch or a digital multiplier.

In the following, the applicants will provide examples of a distributed lock-in amplifier based on switched capacitance circuits and switches (the switches can be controlled by either a digital or an analog signal; the input to the switch is analog in nature). Individual switches can be implemented by a single transistor or by a more complex circuit.

Figure 4:
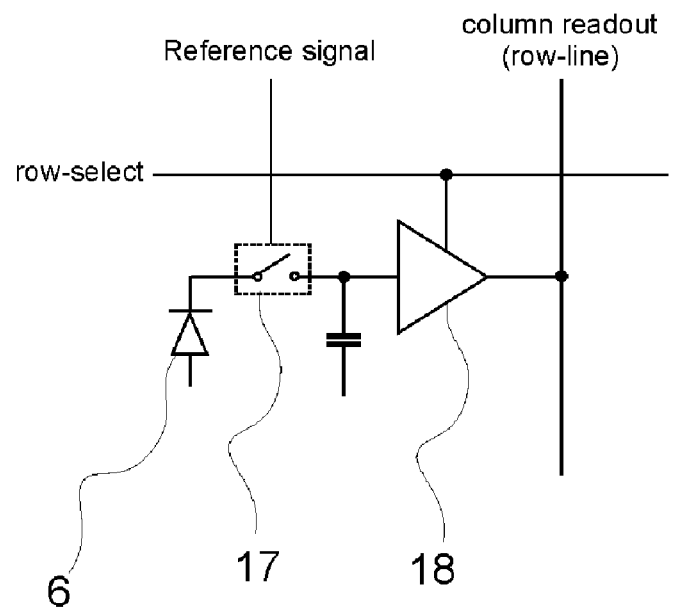
FIG. 4 shows an exemplary mixing technique for use with the embodiment of FIGS. 3A and 3B, where a mixer is implemented by applying a reference signal to a switch.

FIG. 4 illustrates the general principle. A photodiode (6) is mixed by applying the reference signal to a switch (17). Element (18) can be a simple transistor such as transistor (16) of FIG. 3A, or an amplifier/buffer like element (15) of FIG. 3B, that only applies a signal to the column readout if triggered by row-select. A capacitor accumulates the photocurrent. FIG. 4 is intended to convey that each pixel contains at least a switch or analog mixer, an integrating element such as a capacitor (or as seen later more complex integrating circuits) and an element (18) that connects the integrator to the read-out line.

Figure 5:
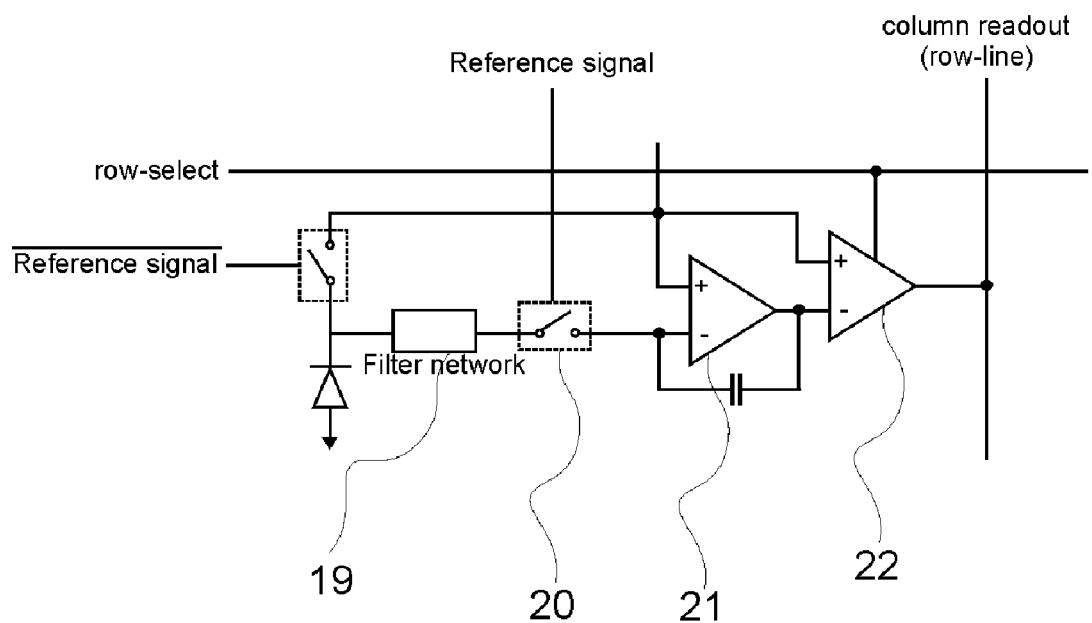
FIG. 5 shows a variation of FIG. 4, where a filter network and an integrator are further provided.
Figure 6:
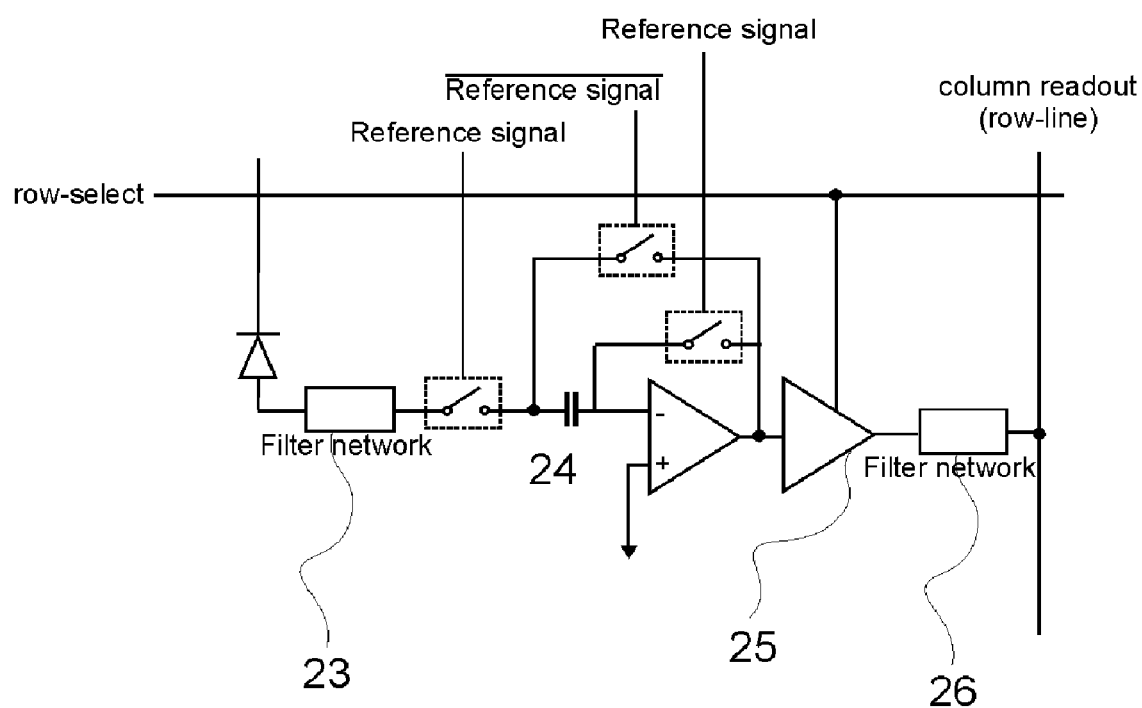
FIG. 6 shows a further variation of FIG. 4, where a switched capacitor sampler-buffer circuit is used.

This circuit can take different forms as exemplified by FIG. 5 and FIG. 6, where an accumulator (FIG. 5) and a switched capacitor sampler-buffer (FIG. 6) are used. In all three cases, further amplifier or filter networks can be placed in the column decoder or later in the circuit. FIGS. 5 and 6 also show how these circuits can properly bias the photodiode.

The circuit in FIG. 5 has the advantage of integrating the signal even if row-select is off. The filter network (19) is ideally a high Q pass-band filter centered on the modulation frequency of light source. At least it filters out the DC component of the reference signal. The switch (20) acts as a mixer. Element (21) is an integrator (for example implemented with a capacitor and a differential amplifier, as shown in the figure). As such it acts both as the low-pass filter (13) of FIG. 2 (it only accumulates the DC component over time) and as an amplifier (10) or (14) of FIG. 2. Element (22) can either be an addressable amplifier such as element (15) of FIG. 2, an addressable buffer, or a simpler switch such as a single transistor (16), as shown in FIG. 3A. Additional filters can be added to the circuit, for example after the integrator (21). Additionally, a reset function can be added (to reset the accumulator, for example by discharging the capacitor in this implementation). Offset cancellation could also be added in case the differential amplifiers show mismatch. This offset cancellation could rely on a feedback loop. It could also calibrated at when the electronic chip is switched on, or calibrated only once after fabrication of the chip and before selling the chip.

The circuit in FIG. 6 relies on a sampler-buffer (24). In this embodiment the sampler-buffer/amplifier comprises three switches, a capacitor and a differential amplifier (see, e.g., "Design of analog CMOS integrated circuits", Behzad Razavi, Mc Graw Hill, 2000). The filter network (23) is ideally a high-Q bandpass filter, at least it filters out the DC component of the signal. Element (25) can be an addressable amplifier such as element (15) described above, or a simple switch such as element (16) described above. The filter network (26) is a low-pass filter. Filter network (26) can also be removed from the pixel and added later in the circuit. Offset cancellation can also be added such as in the case of FIG. 5.

In the above circuits, the timing of the reference signals can be modified a little (small delays) to achieve charge injection cancellation (see, e.g., Razavi, cited above, page 427). Other switched capacitor circuits can be used in the active pixels. For example the sampler-buffer (24) in FIG. 6 can be replaced by a non-inverting amplifier such as shown in Razavi, cited above, page 432. In this way, gain is added to the pixel output. The integrator (21) in FIG. 5 can be replaced by a switched capacitor integrator as described on page 440 in Razavi, cited above.

Part of the lock-in amplifier can be removed from the individual pixel and placed later in the signal path. In that case, it can be either repeated for each column readout (which would still take much less space than if that part would be duplicated for each pixel as there are many pixels on a single column) or it could even be shared by several columns. For example, if a group of columns (activated by a group of row selects) are known to be imaging a specific reservoir of the microfluidic chip corresponding to the detection of a specific molecule, the signals can be added (to a sum 1) before further processing. If a different group of columns is known to correspond to the imaging of a second reservoir detecting a second molecule, the signals of this group of columns can also be added (to a sum 2) and routed to a different output of the adder circuit. Alternatively, the sum 1 and the sum 2 can be time multiplexed on the same adder output. If a subset of columns corresponds to several reservoirs, for example reservoirs that have different y-positions but overlapping x-positions, the summation circuit can add the set of columns corresponding to a given reservoir while at the same time the row addressing circuit can activate the rows corresponding to this reservoir. Then the summation circuit can do the same operation for the next reservoir, cycle through some more reservoirs and then start over (while at the same time the row addressing circuits activates the proper rows in synchronization with the summation circuit). The signals corresponding to the individual reservoir (chamber) can then be time-multiplexed on the same output, or be multiplexed to different outputs. If the output of the multiplexing summation device is still analog, later stages of the regular amplifier or of the lock-in amplifier can be implemented after the summation device. These later stages only need to be laid out once, or a very small number of times. Finally the signal is digitalized with an A/D converter. One example of a good sub-circuit to place at the end of each read-out line, or between the summation device and the A/D converter, is a very high performance filter that could potentially take significant chip real-estate.

The addition of the signals of individual columns can be made dynamical (for example it can be reprogrammed depending on the type of microfluidic chip used). If the signals from the pixels are not amplified with a lock-in, but rather with a simple amplifier, the same principles can be applied. Part of the amplifier can be placed at each pixel, part can be specific to a row, and part can be placed after signals from several rows have been dynamically added. This principle can also be applied to any other circuit in the signal path, although it makes most sense for analog and mixed-signal circuits. After digitalization data treatment can be made by a sequential data processing unit such as a DSP, so that massively parallel circuitry does not represent a problem anymore.

It could be useful in most cases to have at least one accumulator associated to each pixel, so that signals can be accumulated even when not being read at the moment (that is even when read-out is not activated by row-select). The integrator circuit (21) shown in FIG. 5 of the present disclosure or the switched capacitor integrator shown on page 440 of Razavi are particularly suited for this when combined with the filter network (19) that cancels out the DC component of the signal. The integrator then also effectively acts as a low pass-filter because only the DC component created by the mixer (here a switch) will be accumulated over time. The higher frequency component will yield a zero contribution when accumulated over extended periods of time.

The filter network (19) of FIG. 5 can be left out if the mixer (12) of FIG. 2 is a more ideal mixer than a switch (for example a digital switch). If a switch is used the mixer is non-ideal, in that the switch does not multiply the input signal with a sine-wave, but by a periodic function that also has higher harmonics as well as a DC component. Due to this DC component in the multiplying function, DC components in the input signal will also create a finite DC component in the output of the mixer. As the DC component at the output of the mixer is amplified in later stages, and the DC component in the input signal is not part of the "target signal", it should be filtered out prior to the mixer. Because of the higher harmonics of the multiplying function, noise in the input signal at these higher harmonics can also be down converted to the mixer. Thus it can be beneficial if he filter network (19) also cuts off higher frequency noise. Alternatively, a more complex switch can be used that acts as a buffer in the on state and as an inverter in the off state, this then leads to a multiplying function without DC component.

Figure 7:
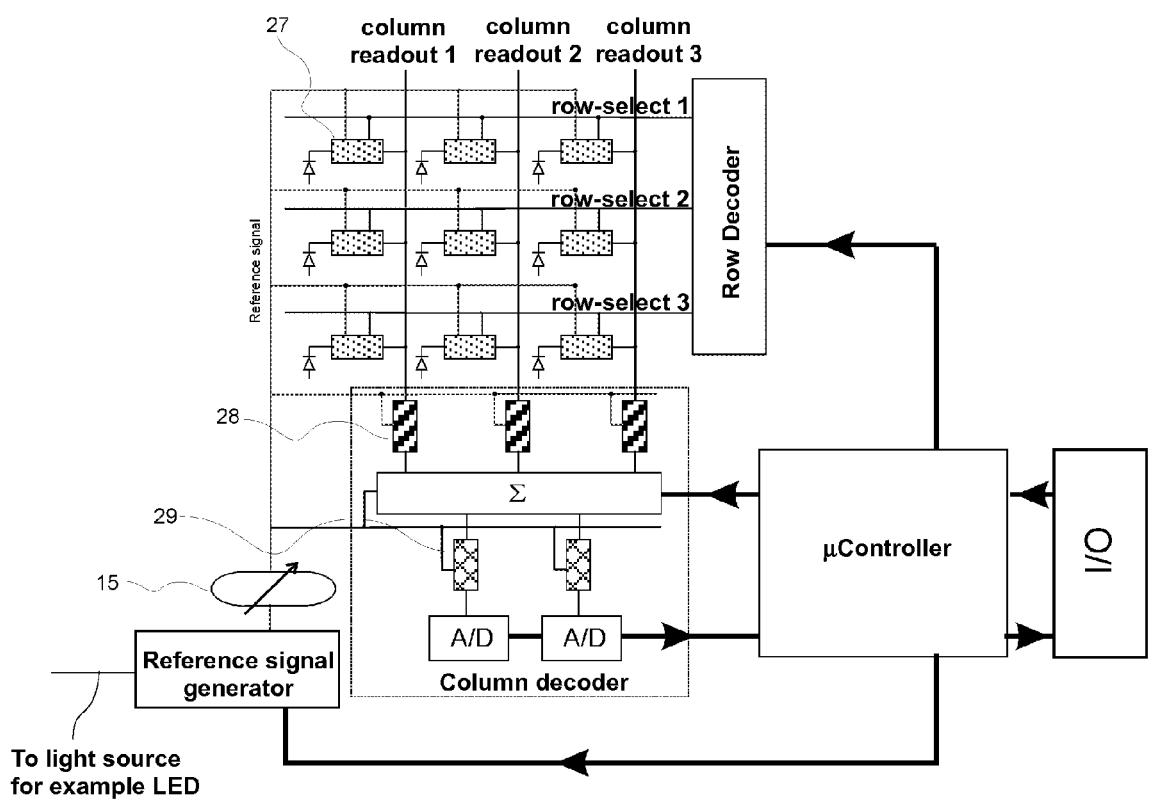
FIG. 7 shows an example of an architecture for the imaging circuit.

FIG. 7 shows a schematic of the chip architecture. A circuit, such as for example a lock-in amplifier, an integrator, or a regular amplifier, is split into three parts, (27), (28), and (29). Element (27) is distributed in the CMOS array (here only 9 pixels are shown in order to simplify the schematic), so that it has to be duplicated for each pixel. Advantages are that the signal can be integrated for every pixel at the same time, that higher signal to noise ratios are achievable at higher speeds. An entire column shares the second portion of the circuit. Finally, individual columns are summed together (summation circuit marked by Σ) and the outputs sent to the third stage (29) of the circuit. There are several outputs to accommodate, for example, a situation where several microfluidic chambers are monitored. Each individual output could correspond to a different chamber (for example to monitor 2 molecules, or to have a detection chamber and a reference chamber to compare to). Alternatively, several output corresponding to several reservoirs can be time-multiplexed onto the same output. Σ can either be programmed once and stay constant over a sustained period of operation (static re-routing), for example in the case where the two chambers (i.e. the detection chamber and the reference chamber) are offset diagonally (that is, the chambers do not share a common row or a common column), or dynamically re-routed to accommodate reservoirs that share a subset of columns. Indeed, if, for example, the two chambers have common columns (but different lines), they cannot be read at the same time. They need to be read sequentially, by changing the state of the row decoder and of the summation circuit. The output of element (29) is sent to an A/D converter, and the data then sent to a micro-controller via a digital bus (marked by a thick line, the arrow indicates the direction of data-flow). A reference signal generator sends a reference signal to the light source and to the components of the lock-in in order to modulate the light source at the same frequency than the reference signal of the mixers. The reference signal is sent to the individual pixels and to the other parts of the circuitry (distributed lock-in amplifier) that necessitates it. A phase shifter (15) ensures that the signal detected by the photodiodes in the pixel array is in phase with the reference signal fed to the mixers.

Note that the reference signal is distinct from the clock of the digital electronics (not shown in the figure), although it could be generated from the clock. The reference signal could also be generated by a voltage controlled oscillator (VCO), an external quartz crystal, or by other means. The micro-controller controls the row decoder, the summation circuit, and optionally the reference signal generator and the phase shifter (15). Finally, the micro-controller is connected via a digital bus to an I/O circuit that handles connection to other chips (and could be part of the microcontroller), or directly implements a communication protocol to communicate with a computer or with the internet, either by cable or with a wireless connection. Alternatively, the data can be stored in a memory (on chip, or on a separate chip in the apparatus), and then be downloaded at a later point of time.

It is understood that the incorporation of subsets of the lock-in amplifiers into the pixel and then addition of the rest of the lock-in amplifier at a later point of the circuit can be implemented independently of the specific architecture of FIG. 7, and that the architecture of FIG. 7 can be applied to pixel arrays without distributed circuits. Even in the extreme case, where the imager where a passive CMOS imager or another type of imager the architecture can be used to obtain data corresponding to one or several microfluidic chambers, while being able to distinguish between these datasets.

FIG. 7 shows an architecture with a classical row decoder/column decoder structure. However all the concepts can be easily generalized to other pixel addressing schemes.

If the output of the individual pixel is a voltage, several rows should be sequentially read even if they correspond to the same chamber. The summation device sums the signals from all the relevant columns at a given point in time. It can also sum the signals from the relevant rows by integrating the signals, or the digital signal processor can do that after A/D conversion.

Because it is usually easier to add currents then voltages, elements (27) and (28) can be chosen to encode the signal as current amplitude modulation. For example, in FIG. 4, element (18) could be a simple switch or a current-current amplifier.

If the output of the pixel is a current, it is possible to read out all the rows pertaining to a given chamber at the same time, as the currents simply add up on the column read-out line. The implementation of the summation device is also easier. If the element (18/22/25) is an amplifier, it can be chosen to be a current-to-current amplifier, or a voltage-to-current amplifier (if the previous stage outputs a voltage). The integrator, or the switched capacitor integrator can be implemented to output a current. Examples of pixels outputting a current onto the read-out line is given, for example, by FIG. 4 if element (18) is implemented by a transistor in the same configuration as element (16) in FIG. 3(a). In order to achieve some current gain (18) can be replaced by a current mirror with the second branch connected to the read out-line.

Figure 16A:
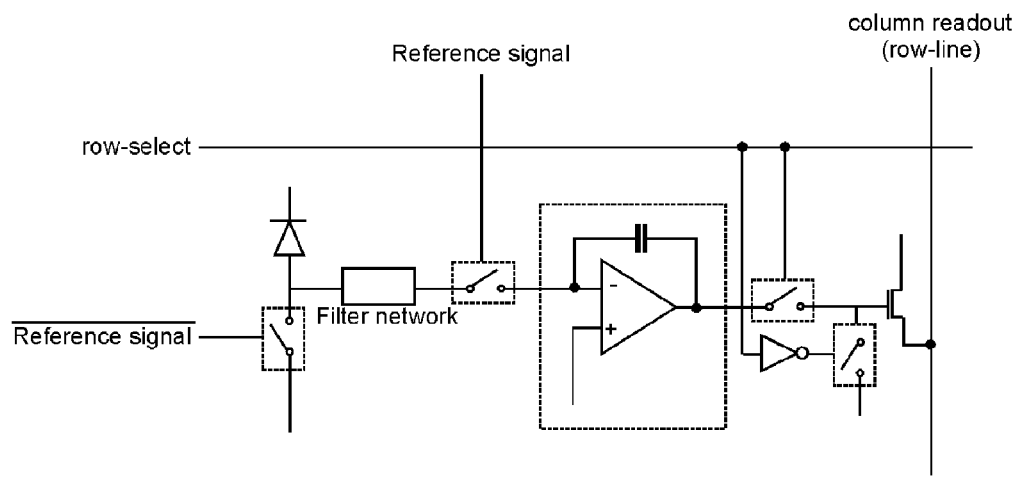
FIGS. 16A and 16B show further embodiments of the circuit of FIG. 5.

Using a configuration as in FIG. 16A incorporating a mixer, a switched capacitor integrator (or regular integrator) and a circuit loading the read-out line with a current has the a advantage over using a plain capacitor, because the pixel can be read without discharging the accumulator. As such, the current status is obtained at every readout, but integration, and as such enhancement of signal to noise, is ongoing. Resetting the accumulator is triggered by an independent reset signal (not shown in figure). On the other hand, in a circuit where the capacitor is directly connected through a switch to the read-out line, reading the circuit also empties the capacitor that accumulates the signal.

Figure 16B:
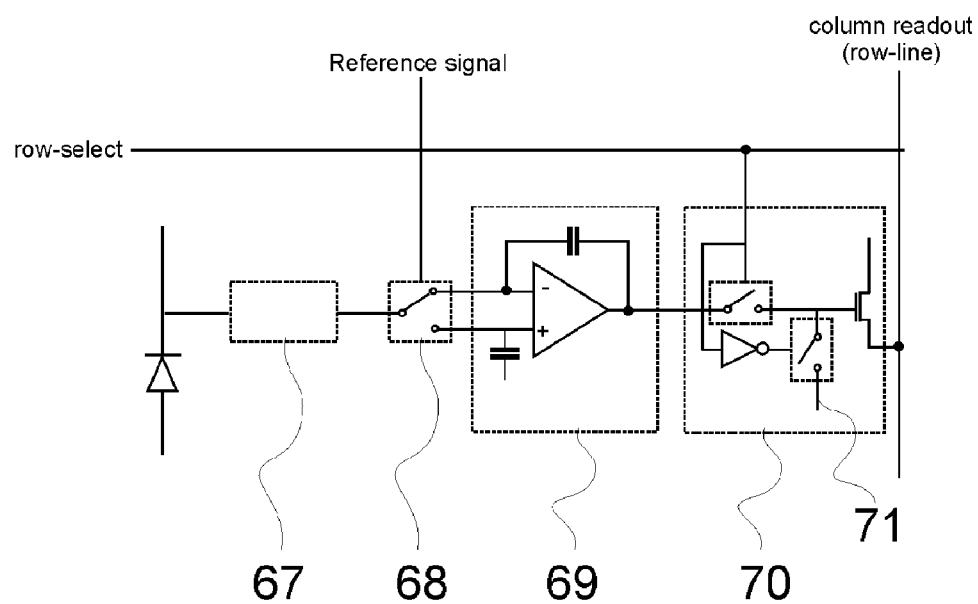

FIG. 16B shows how the filter network of FIG. 16A can be replaced by a subtractor that cancels the DC component of the photocurrent. The subtractor/integrator in FIG. 16B can also be implemented with a switched capacitor circuit in order to properly bias the individual components of the circuit (such as for example the amplifier and the photodiode). The integrator/subtractor can also replace the combination of DC cancellation filter network and integrator in the other circuits. In the circuits described above that do not have an integrator, but that do necessitate a DC cancellation network, a regular subtractor can replace the functionality of the DC cancellation network (for example of the capacitance necessitated in the DC cancellation network is too large). If the switch (68) in FIG. 16B is not perfect (for example if some of the current leaks when the switch is in one of its states), the imperfection can be compensated by adjusting the value of the two capacitors in the integrator/subtractor circuit, to that effect one or both of these capacitors could be implemented by a varactor or other type of adjustable capacitor. Alternatively to adjusting the capacitors, the duty ratio (that is the ratio of on-time to off-time) of the reference signal controlling the switch (68) can be adjusted.

In FIGS. 16A and 16B, (67) is a circuit used to properly bias the photodiode, (68) is a switch, (69) an integrator/subtractor and (70) a circuit that converts the voltage output of (69) to a current that is routed on the read-out line when row-select is on. (70) is optional as the voltage output from 69 could also be directly routed on the read-out line via a switch/buffer, however a circuit like (70) enables the simultaneous read-out of multiple rows and adding the signals. A possible implementation of (71) is shown with two switches and an inverter (the inverted signal could also be provided by the row decoder to simplify the pixel electronics). In this embodiment the bias voltage (71) is chosen so that the transistor shown on the right side is off when its gate is connected to (71). More complicated circuits with the same functionality as (70), that ensure lower noise, higher linearity or additional gain, could also be used. In FIGS. 4, 5, 6, 16A and 16B lines that are unlabeled and left unconnected on one end correspond to a bias voltage.

There are definite advantages in terms of signal integrity and signal to noise in doing a summation of the signals of the individual pixel belonging to the same chamber before A/D conversion. For example, such embodiment is advantageous if the signal of an individual pixel is below the noise floor of the A/D converter. If all the pixels are summed beforehand the noise of the A/D converter will be applied only one to the overall signal (instead of sqrt(n) times, where n is the number of pixel; the square root is due to the fact that noise adds up incoherently). The summed signal can also be way above the noise floor of the A/D converter even if an individual pixel is not above the noise floor. This also applies to the rest of the circuitry. For example, the noise arising from elements (28)

and (29) of FIG. 7 will only be applied once to the signal resulting from a group of pixel, while the noise of element (27) of FIG. 7 will be applied to all the pixels individually. For this reason, the designer should export noisy parts of the system to element (28) and to element (29), if possible. For this reason, it might be beneficial to reduce element (27) to the bare minimum, with a mixer, an integrator (for example a capacitor) and a transistor controlled by the row decoder to connect the output of the integrator to the read-out line.

The summation circuit $\Sigma$, as well as the row addressing circuit and the column decoder, might have to perform quite complex tasks as described above. However, each microfluidic chamber should be monitored over sustained time periods in order to obtain quantitative data (and the concentration of a molecule rather than just its presence) so that the sequence of tasks should be repeated. Instead of sending commands through the bus for every individual task, the sequence of tasks can be programmed into these circuits by the micro-controller before the beginning of the monitoring. The circuits can then cycle independently through the tasks. Because—in accordance with this embodiment—the control part of the circuitry is digital, the individual elements will automatically stay synchronous if started at the same time.

Finally, elements (28) and (29) of FIG. 7 can be combined (at the location of element (28) in FIG. 7), the A/D placed before the summation circuit, and the analog/mixed signal summation circuit replaced by a digital summation. In such a case, the mixer could also be replaced by a digital multiplier placed directly after the A/D or after digital signal summation. Of course, the person skilled in the art will understand that all the digital functionalities can be handled by either a dedicated circuit or by the micro-controller.

All these concepts are applicable to different types of imagers. For example, the CMOS photodiode array can be replaced by an array of avalanche photodiodes to achieve higher sensitivity. BiCMOS is a technology that is particularly promising for this application. The ability to incorporate bipolar transistors enables much lower noise amplifiers in a BiCMOS process as compared to a purely CMOS process. Moreover, growing a silicon thin film on top of the silicon wafer is part of the BiCMOS process. This enables complex vertical implant profiles (this is the reason why the silicon epitaxy is incorporated in BiCMOS in the first place, as the bipolar transistors necessitate the complex vertical implant profile). The bulk wafer can be chosen to have a suitable doping. A series of implants can then be made into this wafer before epitaxy. Then the silicon film is grown with another initial doping. Finally, a series of implantation steps can be made after epitaxy. The availability of complex vertical implantation profiles is extremely useful for the design of high-performance avalanche photodiodes. For example, a highly doped film at the very bottom of the diode is good to reduce series resistance (that gives rise to thermal noise and increases the necessary bias to achieve avalanche under illumination). These complex doping profiles can be obtained in a BiCMOS process because implants can be made before epitaxy at a lower level below the final silicon surface.

The embodiments described above, related to the chip architecture and circuit architecture, can also be applied to a SiGe process. In a SiGe process, lower noise amplifiers than in silicon technology can be designed. Also, the absorption cross-section of light can be enhanced leading to even higher sensitivity. Finally, the avalanche effect requires smaller voltages in SiGe than in Silicon. A particular example of SiGe process that could be used is a CMOS SiGe process or a BiCMOS SiGe process.

For CCD and CMOS imagers used in color cameras, thin film deposition methods have been developed to incorporate filters on top of the individual photodiodes or CCD devices. These filters are typically notch filters in the optical domain that let pass either red, green or blue, so that color information can be recovered by correlating the detected intensities of three adjacent pixels, one for each filter type. The same techniques can be applied to deposit the filter (4) of FIG. 1 on top of the chip (the order of the lens (5) and the filter (4) of FIG. 1 in the light path can be inverted with no consequences on device performance). The filter (4) can be applied to either the microfluidic chip (3) or the imager (6) or be a separate element in between. Moreover, in one embodiment, filter (4) of FIG. 1 can correspond to a multiplicity of filters placed in front of a multiplicity of pixels, the filter being different for different pixel. This opens the opportunity of using detection schemes with different types of dies by placing filters adapted to a particular die in front of a pixel known to be imaging microfluidic chambers in which that particular die will be used. In another embodiment, most pixels have the same filter. However, a few pixels in the mist of the first group of pixels can have no filter or a different filter and are sparsely distributed throughout the first group.

This second group of pixels is used to do a calibration measurement used to calibrate the measurement done by the first group of pixel. For example, the second group of pixels can be used to determine the strength of the light source. In this case, the pixels of the second group can be either unfiltered, or alternatively, filtered with a filter that only lets the light pass that efficiently pumps the dies. Then the light intensity detected by the second group corresponds exactly to the light intensity exciting the dies. Finally, in a third technique, pixels can be left unfiltered so that parts of the microfluidic chip can be imaged by the imager in order to monitor the progression of liquids inside the chip.

In some embodiments methods and devices in the microfluidic chip or circuit (e.g., the microfluidic circuit (3) of FIG. 1) are designed to address the following problems:

1. Actuating the microfluidic chip in a way such that the apparatus around the microfluidic chip requires only a moderate complexity. In particular, actuation mechanisms are disclosed in the present writing that pressurize liquids inside the chip without necessitating external pumps.

2. Loading a sample (and in particular a biological sample) into the microfluidic chip in a user-friendly way, and so that no external pumps are required to push the sample through the switch.

3. Storing reactants on the chip so that truly small amount of reactants can be used (by removing the need for an external pump, the volume of reactants needed also becomes much smaller) and so that the release of these reactants into microfluidic channels can be actuated in very robust ways. The term "sample" refers to the incoming patient sample to be tested, while the "reagents" can be stored as liquid or can be stored in any number of lypholized or gelified states and then reconstituted.

4. Enabling proper calibration of the data collected from the microfluidic chip. In particular, methods and devices enabling proper calibration of the data, also enable gathering quantitative information about molecule concentration rather than merely detecting the presence of a molecule.

5. Designing other devices and methods pertaining to the microfluidic chip.

Microfluidics is often described as a means to produce cheap analytical equipment for the life sciences. The microfluidic devices or chips themselves are very cheap to produce and the amount of chemical reactants needed to perform an analysis is very little. However, one problem is getting the reactants into the microfluidic channel. While the amount of reactant inside the microfluidic chip is very little, much more reactant is needed if the reactant is pumped on chip through a small pipe. In order to provide off-the-shelf microfluidic modules that can be plugged into the analytical device and in order to be able to handle only extremely small volumes, thus avoiding waste of expensive reactants, other filling and storing methods are described hereinafter. Those modules can be plugged in and out to change the test or do a new test.

In order to avoid adding complexity to the analytical device, such as the necessity for several pumps, and in order to avoid cross-contamination, it is beneficial to provide to the user a microfluidic chip with all the reactants already on chip in various sealed chambers. An additional chamber is dedicated to the sample to be analyzed (the sample chamber as opposed to the reactant chambers). The sample chamber can be opened by the user, for example by removing a screw top. The sample can then be introduced into the chamber and the chamber subsequently sealed again by the user, for example by screwing the screw top back on. Sealing devices other than a screw top can be used, such as for example a plug. For the purpose of sealing the sample chamber, a sealing device can be imbedded into the microfluidic chip (the latter typically fabricated with PDMS with its inner channels coated with other materials such as, for example, epoxite to enable ELISA analysis or non-DNA sticking coating). This embodiment is illustrated in FIGS. 8A-8D.

Figure 8A:
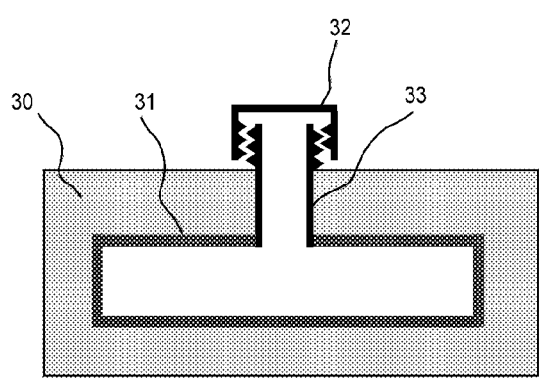
FIGS. 8A-8D show examples of sealing mechanisms for a sample chamber of a microfluidic chip.
Figure 8B:
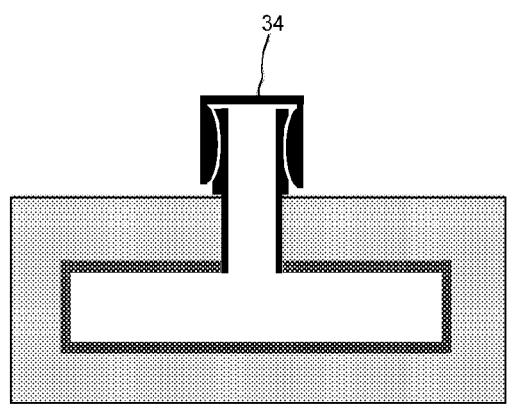
Figure 8C:
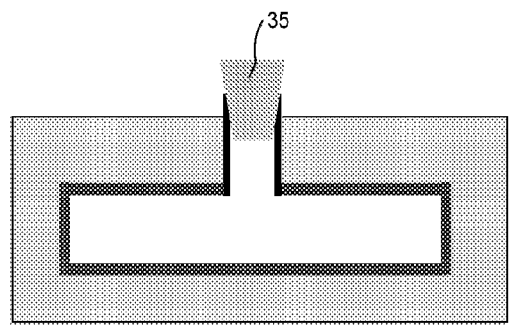
Figure 8D:
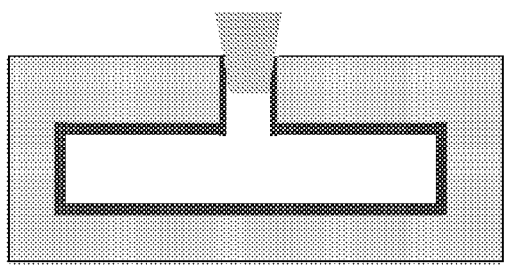

In FIGS. 8A-8D, element (30) shows the material out of which the microfluidic chip is made, for example PDMS. Element (31) represents a second optional material that is coated inside the chamber. Element (33) is an embedded material for the purpose of creating a user-actuated, reversible sealing mechanism such as a screw top (32), a "clip-in" mechanism (34) (FIG. 8B), or a plug (35) (FIGS. 8C and 8D). In some embodiments a clamp can also be used as a sealing mechanism.

Figure 9A:
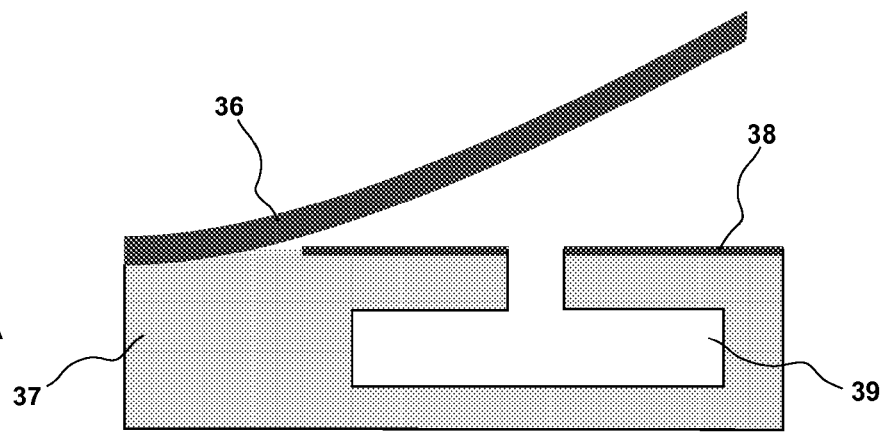
FIGS. 9A and 9B show further embodiments of the sealing mechanism for the sample chamber.
Figure 9B:
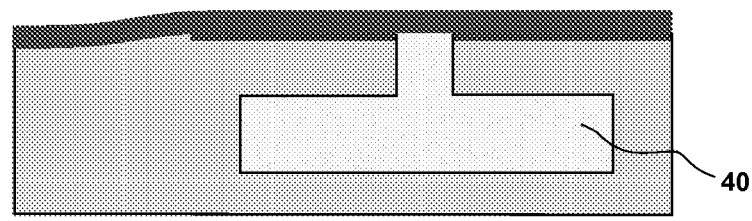

Alternatively, another sealing mechanism can be used as shown in FIGS. 9A and 9B. In these figures, a flap (36), that can be made out of the same material of the bulk of the microfluidic chip (37), or out of a different material, is attached to the chip on the left of FIG. 9A at the time when the chip is purchased by the patient. A coating (38) can be applied to facilitate later adhesion of the flap (36) with the chip (37). In an exemplary embodiment, the user (e.g. a patient using the device for diagnostic purposes) can introduce the sample (40) into the sample chamber (39), and then seals the chamber. The chamber is sealed by pushing down the flap, and then sealing occurs, for example, by applying pressure, heat or UV light (depending on the materials and the adhesion promoter used). Alternatively, a thin "tape-like" layer can be initially attached to the lower side of the flap (36) or on top of the sample chamber (on top of (38) or (39)). After introducing the sample, the user takes off this tape-like film, exposing an adhesion layer that was protected until then. Closing the flap and applying for example pressure, heat or UV radiation will then seal the sample chamber. This technique has the advantage that it is compatible with very small sample chambers, as the flap can be much wider than the chamber. In this configuration, the size of the sample size does not make it harder to seal the chamber correctly.

The reactants are placed inside reactants chambers during manufacturing and theses chambers are sealed after filling. After manufacturing, the microfluidic circuits can be frozen, if necessary, in order to preserve the reactants. A reactant chamber can either be directly connected with a microfluidic channel, in which case the liquid stays inside the chamber because it is frozen, until utilization when it is thawed and pressure applied to the reactant chamber to push the liquid into the channel. Alternatively, the reactant chamber can be connected to a microfluidic channel, but separated from this channel by a thin membrane (made, for example, of PDMS or another material embedded in the PDMS) or a sealed valve (the valve could, for example, be sealed just by natural PDMS by way of PDMS adhesion, when closed). When a sufficient amount of pressure is applied to the reactant chamber, the valve will open or the membrane rupture, letting the reactant flow into the channel. This technique can also be applied to the sample chamber. Operation of a microfluidic chip is described, for example, in U.S. Pub. App. 2006-0263818, which is incorporated herein by reference in its entirety.

Some reactants are better pre-deposited on the surface of the microfluidic channels or on the surface of the chambers in which reactions will occur (the reactors). For example, an ELISA stack requires the surface of the reactor to be coated with an antibody or with an antigen. This coating should be made during manufacturing.

Figure 10A:
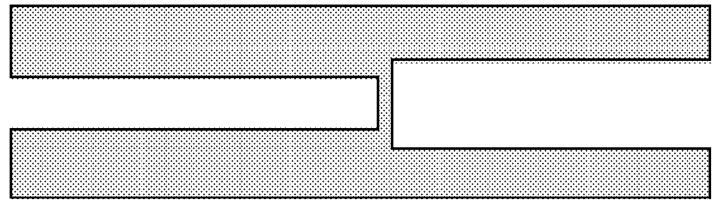
FIGS. 10A and 10B show a valve used to seal a reactant chamber or to gate propagation of the liquid through the chamber. The gating occurs by pressure threshold. Every time the pressure exceeds a new threshold an additional gate (valve or sacrificial membrane) opens and the liquid can propagate further.
Figure 10B:
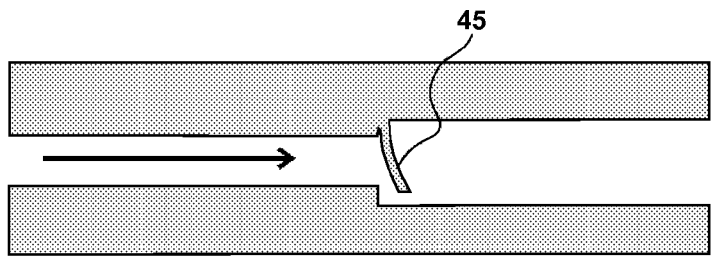

Sacrificial membranes or valves can be further used to control the flow of liquid in the microfluidic chip. The series of elements, valves or membranes (FIGS. 10A and 10B), can be designed in such a way that the valves or membranes open/rupture only when the liquid on one side is above a certain pressure. This pressure can be made to be increasing for elements down the circuit, so that they can be opened in a sequential order and in a controllable fashion. Here the valves are meant to provide a sealing mechanism. A property of the valve that is usually considered undesirable is used that is that the flap of the valve tends to naturally seal with the other PDMS it gets in contact with, effectively sealing the channel. FIGS. 10A and 10B illustrate the principle of a valve acting as a gating mechanism. When the flap (45) is in the position shown in FIG. 10A, the valve is closed. PDMS tends to stick to itself, so that when the valve is closed as shown in FIG. 10A, a pressure threshold needs to be overcome to open the valve. The pressure threshold can be set by modifying the aspect ratio of the flap (45) and by modifying the area of the overlap of the flap with the lower part of the channel (the step in the channel where the sticking occurs).

In some embodiments, particularly suitable for laboratory experiments, microfluidic chips are usually pressure-actuated by connecting the on-chip channels with a small pipe to an off-chip pump. In some embodiments, particularly suitable in applications, e.g diagnostic analysis, to be performed out of lab (e.g. in the home an untrained patient) a completely sealed microfluidic chip (with the exception of of the closure mechanism for the sample chamber that would have to be closed by the user himself after filling) can be provided with simple actuation mechanism that does not introduce undue complexity into the apparatus. This configuration would allow to minimize the complexity involved in connecting the device and the risks of cross-contamination between samples usually associated with the presence of an open channel directly to the pump and to the associated possibility that reactants and samples can flow to the pump and back to another microfluidic chip at a later test.

Accordingly, in some embodiments instead of applying pressure to the liquids in the microfluidic chip with a pump, in both sample chambers and reactant chambers the pressure can be applied by mechanically pushing down on the chip with a piston. This is possible because the fluidic circuits are sealed (rather than left open to connect to the pump). However, it can be extremely difficult to pressurize very small channels in this way, because the mechanical actuator (such as a piston) is a blunt tool that pushes down an entire section of the chip instead of precisely actuating a small chamber or a small channel. This could be remedied by connecting the small channel or the small chamber to a large chamber, the latter being pressurized by the piston. But again, this can be an unsatisfactory solution due to the fact that now a large quantity of liquid is necessary in order to fill the large chamber—this liquid being possibly an expensive reactant or a sparse sample. This can be remedied by having a sealed microfluidic circuit (41) (see FIG. 11A) prefilled during manufacturing with a cheap liquid actuating the microfluidic circuit (42) that is on the "signal-path", that is, containing sample material or reactants etc. The circuit (41) can now comprise a large chamber (43) that is easily actuated by a mechanical actuator (44), such as a piston pushed down by the apparatus onto the microfluidic chip. The circuit (41) can be engineered to precisely actuate the circuit (42), for example by pressurizing a chamber belonging to (42) or by switching on or off a valve controlling the flow through a micro-channel belonging to (42).

Figure 11A:
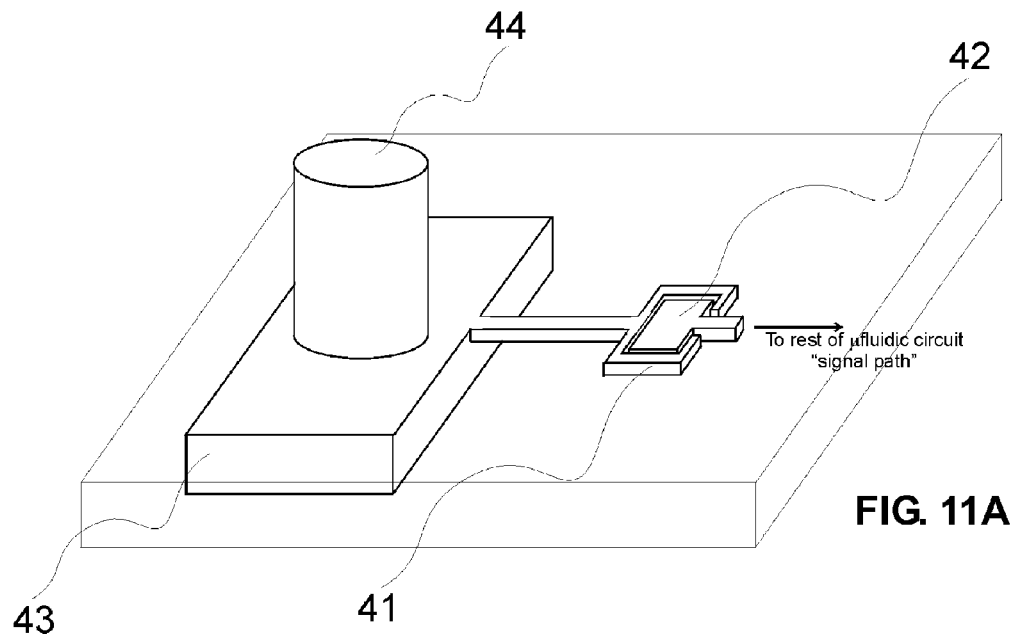
FIGS. 11A and 11B show examples of mechanical actuation of the microfluidic chip.
Figure 11B:
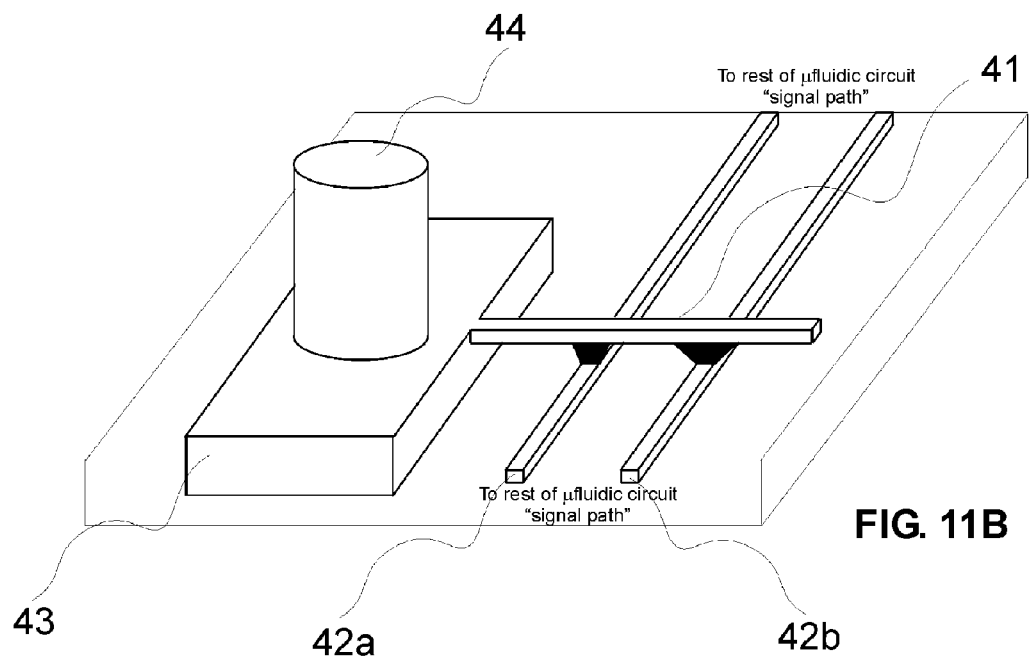

These actuations schemes are illustrated in FIGS. 11A and 11B. In FIG. 11A, the mechanical actuator pressurizes the control circuit (41) that in terns pressurizes the controlled channel (42). The controlled channel (42) comprises a reactant chamber and possibly a sealed valve or a sacrificial membrane between the reactant chamber and the rest of the circuit marked as "To the rest of microfluidic circuit". In FIG. 11B, the mechanical actuator (44) does not control the release of the liquid stored in a reactant chamber, but rather fluid flow later in the microfluidic circuit. The actuator (44) operates by transferring pressure from the controlling circuit (41) to the controlled circuits (42a) and (42b). By changing the aspect ratio of the material between the controlled and the controlling circuit, the pressure of the cuts of either of the controlled circuits can be set, so that the pressure after which channels get cut off can be individually set even if they are controlled by the same channel.

Figure 12A:
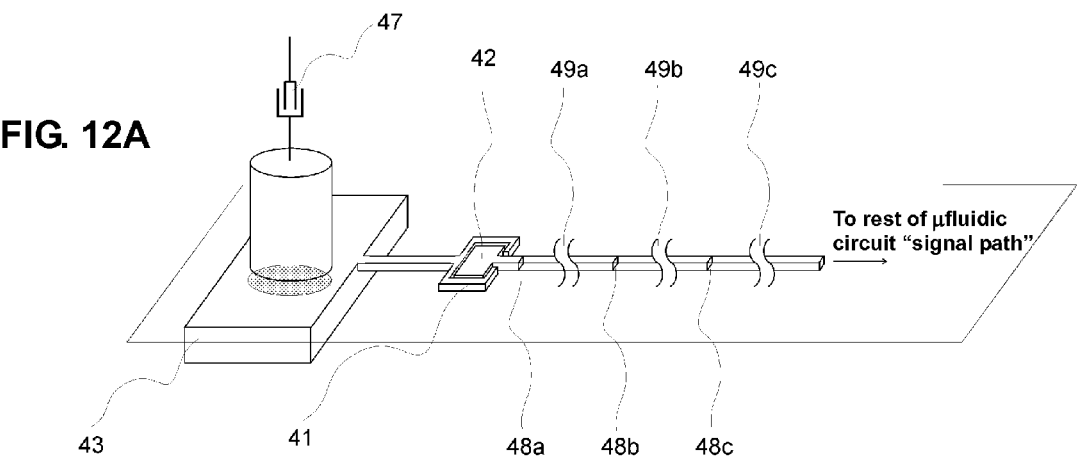
FIGS. 12A and 12B show actuation of the microfluidic chip with pressure control.
Figure 12B:
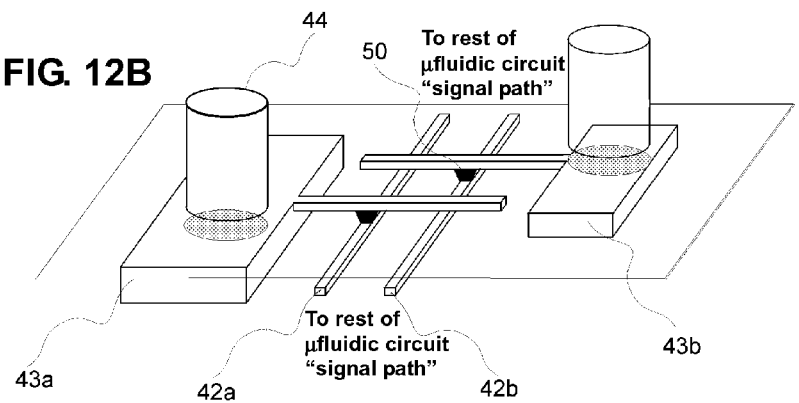

FIGS. 12A and 12B illustrate advanced actuation schemes. Element (47) shows a mechanical actuator that pushes the piston onto the microfluidic channel. Elements (48a), (48b) and (48c) are sacrificial membranes or sealed valves that gate the progression of the liquid in the channel (42). (49a), Elements (49b) and (49c) are sections that are not shown here in which processing of the liquid occurs, for example, mixing with other reactants, heating, reactions etc. There are several ways in which the progression of the liquid through the individual gates can be orchestrated. Element (47) can be programmed to increment the pressure exerted on element (43) by predetermined amounts (or, alternatively, it can be programmed to push the piston down by predetermined amounts). These predetermined amounts can be made dependent on the microfluidic chip inserted inside the diagnostic device (this is explained in detail in a following section). In order to do this, there should be either a position or pressure sensor incorporated into actuator (47), or actuator (47) should be well characterized so that the micro-controller knows what sort of signal to apply to actuator (47) to obtain a given result. In these schemes, the actuator (47) should be continuously tunable or tunable in very small steps.

The cost of the actuator can be reduced if the actuator is set up so that it is associated to a small and/or predetermined set of positions that can be the same regardless of what microfluidic chip is used and regardless of what test is performed. This result can be achieved by adapting the microfluidic chips rather than adapting the positions of the actuator. In some embodiments, this result can be in particular achieved, for example, by adapting the pressure at which the gating elements let the flow pass, so that the pressure to open the gate corresponds to the pressure that is created by the piston when it is moved to its predetermined position. In some embodiments, another method that permits to use the same well characterized gating elements for all the microfluidic circuits, is used. In particular instead of adapting the gating elements, the circuit between the gating elements can be adapted. For example, the channel can be made locally wider or thinner between to consecutive gating elements, or a small chamber can be put between the gating element to modify the volume seen by the liquid (and thus modifying the pressure it will apply on the gating element given a predetermined piston position). If the piston is not set to go to predetermined positions, but to predetermined pressures, a small set of gating elements (one for each pressure) can be directly applied to all the microfluidic circuits without further adapting them.

If a feedback mechanism is incorporated in actuator (47), such actuator can also be used for monitoring purposes. For example, if the sample chamber is not properly sealed and the actuator is used to push a piston on that chamber, or on a chamber connected to a microfluidic circuit used to control the sample chamber, the pressure change that will be observed for a given position increment of the piston (and thus for a given signal sent to actuator (47)) will be different from what is expected. Compliance limits can be set for these pressure variations in order to detect such events. On detection the device can warn the user, discard the measurement, or tag the measurement as being faulty.

If different pressures are necessary or desirable, that can also be obtained from a single actuator setting (that is the actuator is either on or off, pushing or not pushing) if several actuators are used that are connected to separate control channel reservoirs (43a) and (43b) with different geometry (different top membrane size, different top membrane thickness etc.). In this way, very simple actuators can be used with a small number of predetermined settings (for example just on and off in the extreme case), and a multiplicity of pressures can still be obtained on chip, that can then be used to control various devices in the microfluidic chip.

In some embodiments, an alternate way can be used to empty the content of a storage chamber into a channel. This method is particularly attractive for the sample chamber, as a substantial amount of air will usually be sealed inside the chamber along with the sample. Also, some closure mechanisms such as the screw-top are quite bulky, leading to a large chamber with rigid parts (the closure mechanism embedded in the PDMS) making it difficult to empty the chamber with the mechanisms described above.

Figure 13:
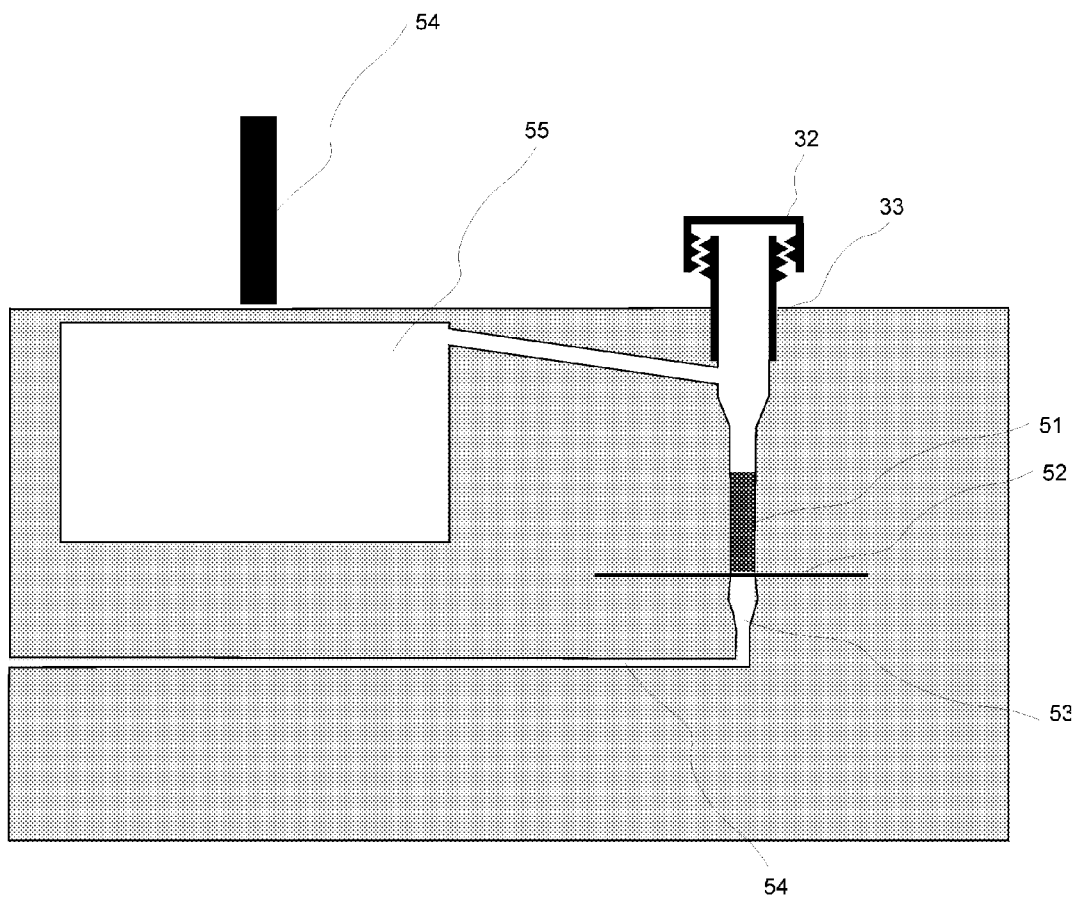
FIG. 13 shows a mechanism to push sample liquid through a filter and into a channel in the microfluidic chip. According to a first embodiment, a piston pushes on an air filled chamber connected to the sample or reactant chamber with a microfluidic channel. However, a further embodiment is also possible, where the piston pushes directly on the sample/reactant chamber. Similar considerations apply to FIGS. 14 and 15.

This is illustrated in FIG. 13. Sample liquid should be pressurized to go into thin channels such as channel (54). Additionally, other obstacles might be on the sample path, such as for example a filter (52) to remove red blood cells and other non plasma component from the blood, as disclosed by Maltezos et. al. in U.S. patent application Ser. No. 11/804,112 which is herein incorporated by reference in its entirety. A mechanical actuator (54) can push on the chamber, or on another chamber (55) filled with air and connected to the sample chamber to increase the pressure and press the liquid through the filter and into the channel. Because air is compressible, as opposed to liquid that is much less compressible, element (55) might need to be large relative to the amount of liquid it is pressurizing.

Figure 14:
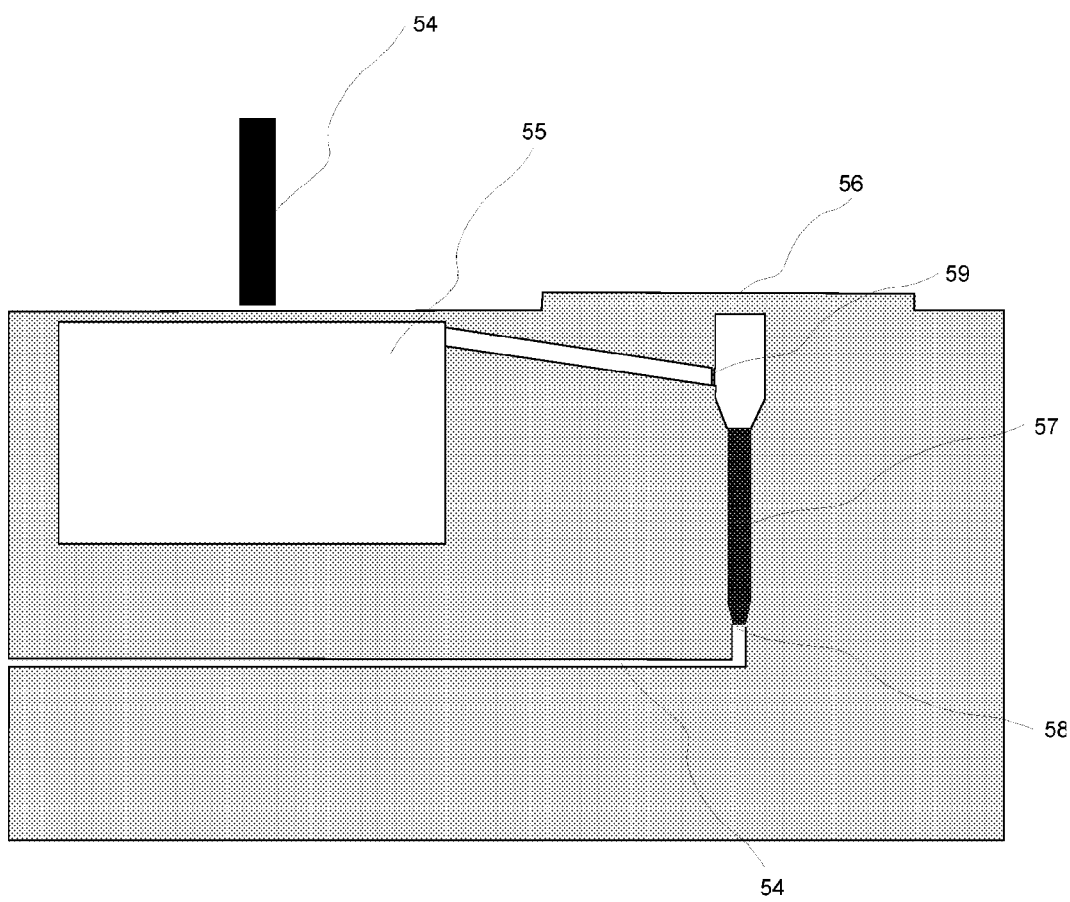
FIG. 14 is a schematic illustration of a mechanism to push reactant into a channel according to an embodiment similar to the one disclosed in FIG. 13.

The same technique can be used for reactants as shown in FIG. 14. In particular, FIG. 14 shows a similar scheme applied to a reactant. After introducing the reactant into the chamber, the chamber is sealed (56) during manufacturing. A sacrificial membrane (58) prevents any of the reactant to go into the channel prior to utilization of the chip by the end user. Typically, the reactant (57) will be frozen. However, to prevent the reactant to flow into the chamber (55) if it is inadvertently unfrozen while the chip is tilted or upside down, an additional sacrificial membrane (59) is added. Both membranes (59) and (58) will only rupture when the actuator (54) compresses the chamber (55). Sacrificial membranes can be replaced by sealed valves.

Heaters can be incorporated into the apparatus to thaw the reactants, either all together, or in a predetermined sequence. In the latter case, heaters (in the forms of resistors) can be placed directly inside the microfluidic chip (that is imbedded inside the PDMS), or placed outside the chip on the microfluidic "cartridge" (described below). Thawing the reactants in a predetermined sequence is a further means of controlling the reactions leading to the detection of the targeted molecule.

The fabrication processes used to build the microfluidic channels can be used at the same time to fabricate cheap optics on the same chip. For example, chambers can be filled with (possible pressurized) liquid during manufacturing, and then sealed, and designed to take the shape of a lens, either naturally or under the action of the pressurized liquid. The index contrast between the liquid and the surrounding material (typically PDMS) then gives rise to the lensing effect.

Chambers can be filled and sealed with liquids during manufacturing that are neither participating to the detection reaction itself, nor used to activate other channels, but have a separate function all together:

A chamber can be filled with a die (activated—that is it does not need to undergo enzyme treatment to start luminescence as in the ELISA stack) that either emits light at the same wavelength then the die used in the ELISA stack, or emits at a wavelength that the filter (4) also lets through. This die will then be imaged by the detector array (for example CCD or CMOS imager). This can be used for calibration purposes, for example to normalize out device to device variations in the optical power emitted by the light source Alternatively, a second detector can be placed before filter (4), and its detected power used for normalization. In this way, however, a second detector is not needed.

Furthermore, a chamber filled with such a die can be used as a light source that can be monitored by the detector (6) shown in FIG. 1. This can be useful to monitor the progression of the testing process. For example, a microfluidic channel can be designed to be below such a chamber, between the chamber and the detector. When fluid fills the cavity the amount of light received by the detector will change, and the image seen by the detector will change (as the channel is illuminated by the chamber). Thus filling of the channel can be detected.

A chamber filled with die that is imaged by the imager or detector (6) can also be used as a marker for position control (in order to tell the electronics where exactly the microfluidic chip is located) or for identification purposes (A given set of markers might identify a chip as a specific chip, the sequence of actuation and analysis the electronics then need to perform being programmed into the diagnostic device).

Also, these pre-activated dies can be used to calibrate the electronics, such as for example the offset cancellation in the lock-in stages, the amplifier gain etc.

Other problems can impact the reliability of the diagnostic tool, for example variations in the ambient temperature that accelerate or decelerate the reaction, or aging of the reactants. It is very useful to be able to monitor these variables. For some applications, it is not only important to be able to monitor whether a molecule is present, but also its concentration in the sample and in particular a biological sample. In order to monitor this concentration, it is important to either have tight control over the speed of the reaction activating the enzyme, or to be able to normalize out the other factors. Indeed in a technique such as the ELISA stack, it is the time dependency of the fluorescence that reveals a concentration.

The calibration chambers can for example be the locus of an ELISA reaction with a liquid containing the detected antigen/antibody. The fluorescence of that chamber, and the fluorescence ramp rate of that chamber, can then be used as a calibration reference.

Alternatively, a calibration chamber can be the locus of a reaction based on reactants with well characterized aging behavior that yields variations in the fluorescence depending on the aging of the reactants. This can then be used to check whether the preemption date of the chip is past.

The calibration chamber can be the locus of a reaction that yields fluorescence detectable by the imager, the intensity and rate of change of the fluorescence being very susceptible to temperature. This can then be used to normalize out the effect temperature will have had on the actual reaction that tests for the target molecule.

In some embodiments, a given microfluidic chip can only be used to perform a finite number of tests. After these tests, it will need to be discarded and replaced by another microfluidic chip. To facilitate swapping the chips in and out, both to replace them when one chip needs to be discarded and to replace them by another chip in order to perform a different type of test, the microfluidic chips can be incorporated in a pluggable module referred hereafter as "cartridge". A cartridge comprises at least a microfluidic chip and a mechanical apparatus to insert the chip into the diagnostic device. The mechanical apparatus could for example be a rail combined with a locking system. The locking system does not need to be user-operated, it can simply click into place so that a certain amount of force is necessitated to remove the cartridge and so that the cartridge is stabilized in its position. Because signals are detected with an imager, the locking does not need to be extremely precise, as small displacements can be easily corrected by the software or by the chip hardware by performing basic pattern recognition.

The cartridge can contain further elements, such as the exemplary elements illustrated below:

- An electronic chip that connects to the analytical device once the cartridge is inserted. This electronic chip could store information about the microfluidic chip carried by the device, such as type of microfluidic chip, as well as the sequence of tasks, such as actuations, detections, heat cycles etc. that need to be performed by the analytical device in order to perform a given test (e.g. a diagnostic test). If a chip is contained on the cartridge it should also store preemption date of the cartridge.
- A temperature control system. As mentioned above the temperature control can be partially incorporated in the microfluidic chip itself, for example in the form of resistors imbedded in the PDMS matrix. However, the temperature control in the form of heaters and/or Pelletier junctions can also be incorporated in the cartridge but outside the microfluidic chip itself. In some embodiments, this solution might be more costly than incorporating it in the analytical device (but outside the cartridge), because it will be discarded every time the cartridge will be discarded. However this configuration will be beneficial if different types of microfluidic chips need very different temperature control schemes.
- A set of optics, in particular filters. In order to make the diagnostic device compatible with different sets of dies that emit light at different wavelengths, the filter (4) (see FIG. 1) should be adapted. One way to do this is to incorporate the filter into the cartridge so that it gets swapped together with the microfluidic circuit. It is also useful to have the filter on the cartridge if it is not filling the entire area, but leaving some areas free so that part of the microfluidic chip can be imaged for monitoring of fluid progression. That configuration might change from microfluidic chip to microfluidic chip.

Incorporating a temperature control system and/or optics into the cartridge, makes the cartridge much more expensive. In order to make the diagnostic device modular, that is filters and heating systems that can be swapped to accommodate different microfluidic chips, a second swappable module (hereinafter referred to as the module) can be introduced that incorporates an optical filter and/or a temperature control system and possibly other functionalities. The cartridge will be discarded every time a microfluidic chip needs to be replaced, but the module will only be swapped when the type of tests performed or the type of cartridges being used necessitate the change. Moreover the module will be reusable, so that of the previous series of tests needs to be performed again it can be swapped back in.

When a different type of cartridge or a different module is being used, the sequence of tasks that need to be performed by the diagnostic tool will change. For example the position of the reactors on the microfluidic chip might change, so that the relevant data has to be collected from different parts of the imager. The summation circuit of FIG. 7, the microcontroller and other electronics then should be reprogrammed. Also the actuation scheme and the temperature control schemes might change and need to be reconfigured etc. This reconfiguration of the device can be achieved by various means including the following exemplary means:

- The program can be stored on a chip located on the cartridge or on the module and then downloaded by the other elements of the device.
- A memory element in the analytical device (on the imager chip or on a separate chip) can store the programs for all the compatible cartridges. The cartridge then only needs to be identified in order to activate the program. Identification of the cartridge could be obtained by means of a simple chip on the cartridge (that now only needs to store the type of cartridge instead of an entire program) or by RF-ID contained in the cartridge. The user could dial in the type of cartridge, either by typing it on a computer with which the device communicates, or directly in the device if such an I/O functionality is integrated (for example by setting a series of switches to dial in a cartridge code).
- The program could be downloaded from a computer, or directly from the internet, depending on how the analytical device is configured.
- Hybrid solutions. For example, all the programs for the compatible cartridges at the time of manufacturing could be stored in the analytical device. If a new type of cartridge is released, or if the device is upgraded to be made compatible with other cartridges (this compatibility does not need to be due to physical reasons, it can be linked to marketing strategy), the corresponding program could be added to the databank by downloading it from a computer, from the internet, or from a pluggable device (such as a USB memory device). The chip containing the programs could also be swapped out, either at a service center or at the end users home if an adequate mechanism is built in.
- If the device is marketed with a market segmentation strategy all the relevant programs can be stored in the chip, but the use of certain type of cartridges artificially deactivated. Upgrading the device, for example by paying a fee on the Internet portal, could then activate this functionality.

Further mechanisms can be incorporated into this analytical device by incorporating a stripped down GPS system and only allowing it to operate in certain region of the planet, or by monitoring the location through the Internet by checking the IP number. It could also be required for the end-user to log in on the portal in order to make the device operable or in order to access the data. Those mechanisms might be particularly suitable in applications wherein the analytical device is used for medical purposes (e.g. diagnostic purposes).

Figure 15:
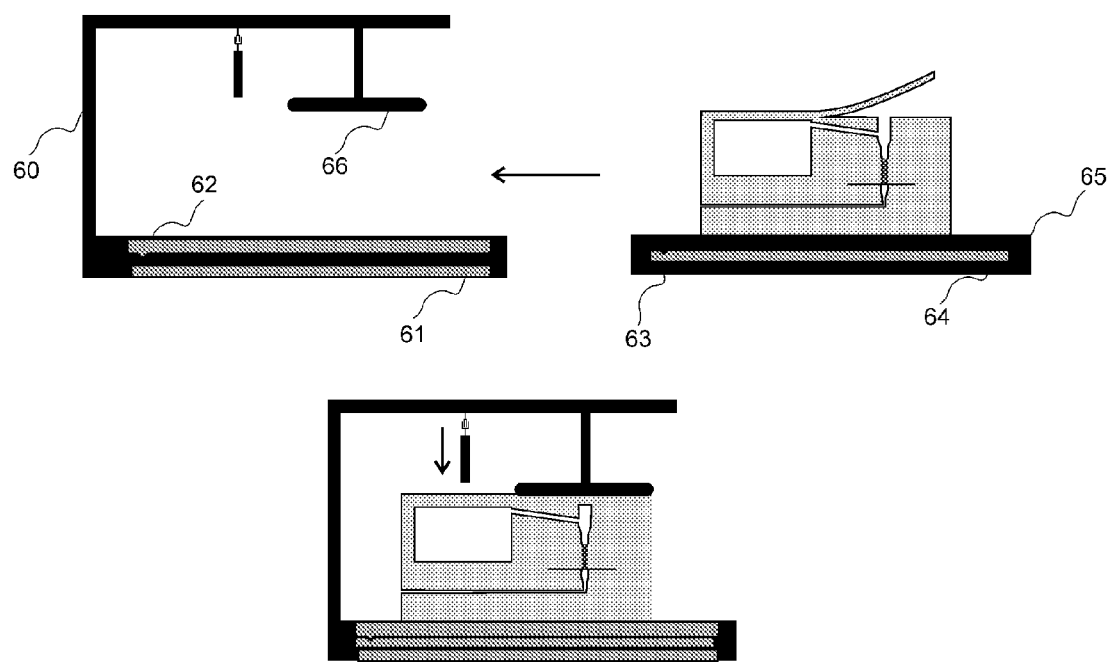
FIG. 15 shows an embodiment of a rail system and sample chamber sealing mechanism.

In some embodiments, the frame of the diagnostic device can be designed in such a way that when the cartridge is inserted into the device, the flap is automatically pushed down, as shown in FIG. 15. This configuration has the further advantage of simplifying the sealing of the flab to the bulk part of the microfluidic chamber. In the configuration of FIG. 15, the element (66) that pushes down the flap can also contain a heater or other additional sealing mechanisms intended to seal the microfluidic chip. However, PDMS tends to naturally stick to PDMS so that the pressure exerted on the flap by (66) can be sufficient to seal adequately the chamber without further actuation. The pressure is simply created by the tight fit of the cartridge within the frame of the diagnostic device. Optionally, element (66) can be actuated to push down once the cartridge is completely introduced. Element (66) is shown with rounded edges so as to avoid damaging the microfluidic chip when introduced into the diagnostic device.

In FIG. 15, element (60) is the frame of the diagnostic device, element (61) is the rail system on the diagnostic device, element (62) the clip-in mechanism on the diagnostic device, element (63) the clip-in mechanism on the cartridge, element (64) the rail system on the microfluidic device, element (65) the substrate of the cartridge and element (66) the element that pushes down the flap. The rail system and clipping system can be equipped with a mechanism to detect the "clipped-in" condition, such as for example an electrical connection from one rail system to the other that is close when clipped-in, or a switch on the analytical device that is actuated when the cartridge is introduced. When the cartridge is introduced, the programmed sequence of tasks can start, for example, the flap can be thermally sealed or the piston (54) can push onto the chamber (55) to pressurize the biological sample and push it into the microfluidic channel.

The analytical device can comprise a sterilization mechanism that will be activated upon removal of the microfluidic cartridge. This sterilization mechanism also destroys the residual bio-molecules in the device. It can be implemented for example by heating up the interior of the apparatus to high temperature.

It is to be understood that the disclosure are not limited to particular configurations or the device, samples, applications or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the device(s) and methods herein disclosed, specific examples of appropriate materials and methods are described herein.

The description set forth above is provided to give those of ordinary skill in the art a complete disclosure and description of how to make and use the embodiments of the devices, systems and methods of the disclosure, and are not intended to limit the scope of the disclosure. Modifications of the above-described modes for carrying out the device(s) and methods herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

A number of embodiments of the device(s) and methods herein disclosed have been described. Nevertheless, it will be understood that various modifications may be made without departing from the spirit and scope of the disclosure. Accordingly, other embodiments are within the scope of the following claims.

What is claimed is:

1. An apparatus for analysis of a sample, comprising:
   a microfluidic chip containing dies, wherein the microfluidic chip comprises:
      a first chamber; and
      a second chamber connected with the first chamber;
   a piston configured to apply pressure to the second chamber by mechanically pushing down on the microfluidic chip, wherein the second chamber transfers some or all of the pressure applied by the piston to the first chamber;
   a light source to emit light for illumination of the microfluidic chip, wherein the light source is modulated and thus emits modulated light;
   a first optical filter placed between the light source and the microfluidic chip;
   a second optical filter; and
   a detector to detect the light passing through the second optical filter, the second optical filter being placed between the light source and the detector, wherein the detector comprises a passive or an active CMOS or CCD array, and
   a lock-in amplifier, the lock-in amplifier being at least partially distributed along the CMOS or CCD array, wherein the lock-in amplifier comprises switched capacitance circuits and switches,
   wherein presence of target molecules in the sample activates and/or immobilizes a die at a position detectable by the detector, the second optical filter allows passage of the light from the dies once activated and/or immobilized by the presence of the target molecules, and the first optical filter prevents passage of said light.

2. The apparatus of claim 1, wherein the detector is selected from the group consisting of photodiodes, a charge coupled device, a CMOS imager, a phototransistor and a photomultiplier tube.

3. The apparatus of claim 1, further comprising one or more lenses to image an output of the second optical filter on the detector.

4. The apparatus of claim 1, further comprising one or more reflectors to reflect back light otherwise not absorbed by the dies.

5. The apparatus of claim 1, said apparatus being a handheld diagnostic tool.

6. The apparatus of claim 1, wherein the microfluidic chip comprises a sample chamber to contain the sample to be analyzed.

7. The apparatus of claim 1, wherein the microfluidic chip further comprises a reversible sealing mechanism to seal the first chamber, the reversible sealing mechanism being selectable from the group consisting of a screw top, a clip-in mechanism, a plug, a flap and a clamp.

8. The apparatus of claim 1, wherein the microfluidic chip further comprises sacrificial membranes or valves to control flow of liquid in the microfluidic chip, the membranes or valves opening when liquid is above a certain pressure.

9. The apparatus of claim 1, wherein the second chamber is a reactant chamber.

10. The apparatus of claim 1, wherein the first chamber is smaller than the second chamber.

11. An apparatus for analysis of a sample comprising a plurality of target molecules, the apparatus comprising:
    a microfluidic chip containing dies, the microfluidic chip comprising a plurality of reservoirs, wherein each reservoir is configured to receive the sample;
    a light source to emit light for illumination of the microfluidic chip;
    at least one optical filter; and
    a detector configured to detect the light passing through the at least one optical filter and configured to output a plurality of signals, each signal in the plurality of signals being associated with a particular reservoir, wherein the detector comprises:
       an array of pixels, wherein each pixel is associated with one reservoir in the plurality of reservoirs, and
       a plurality of summation circuits, wherein each summation circuit adds an output from one or more pixels in the array of pixels associated with the particular reservoir to generate a signal in the plurality of signals,
    wherein presence of a target molecule in the sample activates and/or immobilizes a die at a position detectable by the detector, each optical filter in the at least one optical filter allows passage of the light from the dies once activated and/or immobilized by the presence of the target molecule.

12. The apparatus of claim 11, further comprising a lock-in amplifier associated with the detector, wherein the lock-in amplifier comprises a mixer connected with a low pass filter.

13. The apparatus of claim 11, further comprising an impeding optical filter, wherein the impeding optical filter prevents passage of the light from the dies once activated and/or immobilized by the presence of the target molecule.

14. The apparatus of claim 11, further comprising a lock-in amplifier, the lock-in amplifier being at least partially distributed along the array of pixels, wherein the lock-in amplifier comprises switched capacitance circuits and switches.

15. The apparatus of claim 11, wherein each pixel in the array of pixels is associated with one optical filter in the at least one optical filter.

16. The apparatus of claim 1, wherein the second chamber is filled with air.

* * * * *